United States Patent
Bhat et al.

(10) Patent No.: US 8,377,435 B2
(45) Date of Patent: Feb. 19, 2013

(54) ANTIBODY INDUCED CELL MEMBRANE WOUNDING

(75) Inventors: Neelima M. Bhat, Los Altos, CA (US); Marcia M. Bieber, Los Altos, CA (US); Nelson N. H. Teng, Hillsborough, CA (US); Martin E. Sanders, Hillsborough, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 756 days.

(21) Appl. No.: 11/267,935

(22) Filed: Nov. 4, 2005

(65) Prior Publication Data

US 2006/0153854 A1    Jul. 13, 2006

Related U.S. Application Data

(60) Provisional application No. 60/625,398, filed on Nov. 5, 2004.

(51) Int. Cl.
- *A61K 39/395* (2006.01)
- *A61K 39/00* (2006.01)
- *C07K 16/00* (2006.01)
- *C12P 21/08* (2006.01)

(52) U.S. Cl. ............... 424/130.1; 424/141.1; 424/142.1; 424/153.1; 424/155.1; 530/387.1; 530/388.1; 530/388.7; 530/388.73; 530/388.8

(58) Field of Classification Search ........................ None
See application file for complete search history.

(56) References Cited

U.S. PATENT DOCUMENTS

| | | | | |
|---|---|---|---|---|
| 5,417,972 | A * | 5/1995 | Bhat et al. ................. | 424/137.1 |
| 5,593,676 | A * | 1/1997 | Bhat et al. ................. | 424/137.1 |
| 2002/0028178 | A1* | 3/2002 | Hanna et al. ................. | 424/1.49 |
| 2002/0090366 | A1* | 7/2002 | Browning et al. ........... | 424/94.1 |
| 2005/0112130 | A1* | 5/2005 | Bhat et al. ................. | 424/155.1 |

OTHER PUBLICATIONS

Bhat et al. (Critical Review in Oncology/Hematology. 2001. 39:59-68).*
Chen et al. (Mol. Immuol. 1998, 35:195-205.*
Kaiser (Science, 2006, 313, 1370).*
Bhat et al. (Clin. Exp. Immunol. 1997, 108:151-151-159).*
Bhat et al. (Clin. Exp. Immunol. 1996, 105:183-190).*
Taber's Cyclopedic Medical Dictionary (1985, F.A. Davis Company, Philadelphia, p. 274).*
Busken, C et al, (Digestive Disease Week Abstracts and Itinerary Planner, 2003, abstract No. 850).*
Krontiris and Capizzi (Internal Medicine, 4th Edition, Editor-in-chief Jay Stein, Elsevier Science, 1994 Chapters 71-72, pp. 699-729).*
Carter, S. K. et al. (Chemotherapy of Cancer; Second edition; John Wiley & Sons: New York, 1981; appendix C).*
Carey et al. (J. Immunol. 2001 166: 1618-1626).*
Bhat et al. (Clin. Immunology and Immunopathology 1997, 84:283-289).*
National Cancer Institute (Dictionary of Cancer Terms, www.cancer.gov, phase I trial, Mar. 26, 2009).*
Janeway et al. (Immunobiology 5, 2001, Garland Science, Figure 9.3, 12.2, and 13.1).*
Bhat et al. (Scand. J. Immunol. 2000 51: 134-140).*
Sigma-Aldrich (Sodium Azide, Material Safety Data Sheet, 2009).*
Cohen (Int. J. Radiat. Oncol. Biol. Phys. 1987, 13:251-8).*

* cited by examiner

*Primary Examiner* — Peter J Reddig
(74) *Attorney, Agent, or Firm* — Birgit Millauer, Esq.; Chao Hadidi Stark & Barker LLP

(57) ABSTRACT

Compositions and methods for inducing cell membrane wounding, cell permeabilization and cell killing are provided. The composition comprises a polyvalent agent that binds to a highly expressed cell surface antigen present on the surface of a cell. Preferably, the cell surface antigen is associated with the cytoskeleton of the cell. A preferred polyvalent agent is an IgM, and enhanced cell wounding and killing can be provided by the addition of a crosslinking agent. At sublethal concentrations in vivo, the cell wounding antibodies permeabilize cells and dramatically enhance response to chemotherapeutic agents, even in patients refractory to the chemotherapeutic agents.

20 Claims, 11 Drawing Sheets

V4-34 encoded mAbs bind Primary B cell Lymphomas and Leukemias of all categories

| Specimen # | Diagnosis | MCF* |
|---|---|---|
| 1 | Diffuse Large cell Lymphoma | +++ |
| 2 | Diffuse Large cell Lymphoma | +++ |
| 3 | Follicular Lymphoma | ++ |
| 4 | Follicular Lymphoma | ++ |
| 5 | Follicular Lymphoma | ++ |
| 6 | pre B leukemia | +++ |
| 7 | SLL; leukemic stage | +++ |
| 9 | T cell lymphoma | - |
| 10 | Diffuse Small Cell Lymphoma | +++ |
| 11 | Diffuse Large cell Lymphoma | +++ |
| 12 | Lymphoblastic (B); ALL stage | +++ |
| 13 | Diffuse Large cell Lymphoma | ++ |
| 14 | Small Lymphocytic Lymphoma | +++ |
| 15 | Mantle Cell Lymphoma | +++ |

*MCF: Mean Channel fluorescence. Cells were stained 216-biotin (1 µgs/ml) and avidin-FITC

FIG. 1

VH4-34 encoded mAbs bind and kill human B cell lines

| B cell line | B cell stage | B cell line | B cell stage | B cell line | B cell stage | B cell line | B cell stage |
|---|---|---|---|---|---|---|---|
| Nalm-6 | Pre-B | Arent | mature-B | Daudi | Burkitt's | VB5 | lymphoblastoid |
| Reh | Pre-B | OCI-Ly8 | mature-B | Ramos | Burkitt's | MF4 | lymphoblastoid |
| | | Sup-B8 | mature-B | | | JB7 | lymphoblastoid |

FIG. 2

Vincristine and mAb 216 mediated Cytotoxicity is Synergistic

| | | Live Cells $10^5$/ml | % killed |
|---|---|---|---|
| Nalm-6 | control | 11 | |
| | 216 | 7.1 | 35 |
| | VCR 2ng/ml | 5 | 54 |
| | 216 + VCR | 0.28 | 97 |
| | | | |
| | control | 13 | |
| | 216 | 10 | 23 |
| | VCR 0.2ng/ml | 13 | 0 |
| | 216 + VCR | 6 | 53 |
| REH | control | 8.6 | |
| | 216 | 4.6 | 46 |
| | VCR 2ng/ml | 4.2 | 51 |
| | 216 + VCR | 0.45 | 94 |
| | | | |
| | control | 13 | |
| | 216 | 11 | 15 |
| | VCR 2ng/ml | 7.7 | 40 |
| | 216 + VCR | 0.9 | 93 |
| SUP B15 | control | 5.1 | |
| | 216 | 3.6 | 29 |
| | VCR 2ng/ml | 2.8 | 45 |
| | 216 + VCR | 1.5 | 70 |

Three ALL cell lines with different genotypes and phenotypes :
Nalm-6 : pre B,CD19 +,10+, HLA DR+, no sm or cy Ig, diploid, doubles in 30h
REH: pre B,CD19 +,10+, 20+, DR+, no Ig TEL_AML1 fusion gene, doubles in 45-50h
SUPB15 : pre B,CD19 +,10+,13+,34+,37+, DR+, cyto. IgM/k pos.,BCR-ABL gene,doubles in 60-70 h
Cells are counted with a hemocytometer using trypan blue to determine total cell count. The cells are then analyzed on a flow cytometer using propidium iodide (PI) staining to get an accurate percentage of dead cells.
The control cells are used to gate on live cells and this gate determines percent alive for each sample.
Cell count is necessary as there is cell lysis/loss during the incubation and this is not reflected in percent dead when analyzed.

FIG. 4

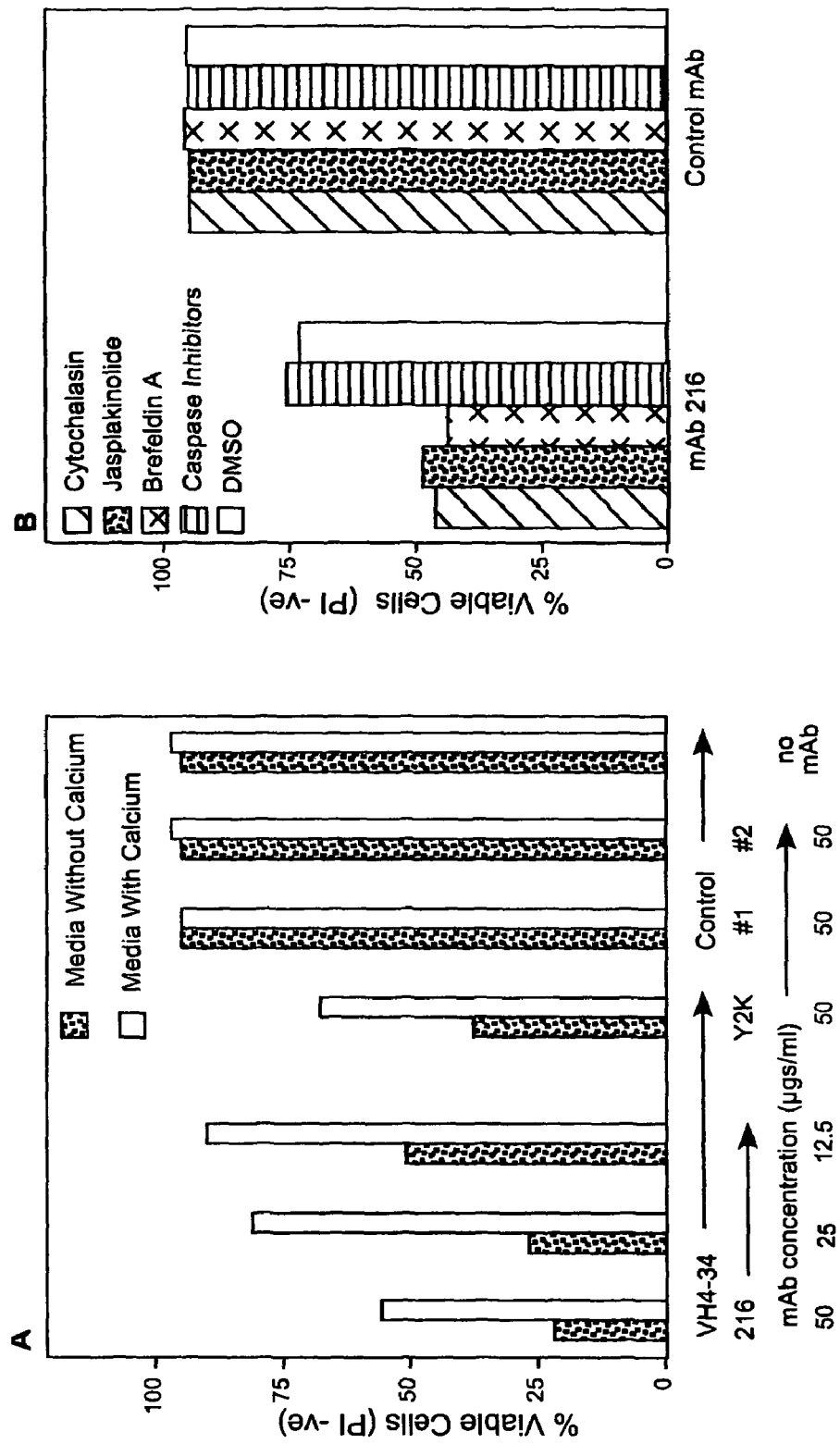
FIG. 6 A and B

ANTIBODY INDUCED CELL MEMBRANE WOUNDING

CROSS-REFERENCE TO RELATED APPLICATIONS

This application claims priority from U.S. Provisional Patent Application No. 60/625,398 filed on Nov. 5, 2004, which is incorporated herein by reference. This application is related to U.S. patent application Ser. No. 10/982,698, also filed on Nov. 5, 2004, which is incorporated herein by reference.

FIELD OF THE INVENTION

This invention relates generally to compositions and methods for permeabilizing cells, treating cancer and autoimmune disorders, and the like.

BACKGROUND OF THE INVENTION

Cell membrane wounding is a disruption of the plasma membrane of cells, and is generally a survivable event. Cell membrane wounding is a common occurrence in mechanically active mammalian tissues such as the endothelial lining of the aorta or gastrointestinal tract, skin epithelia or myocytes of cardiac or skeletal muscle, and has also been demonstrated during the invasion of cells by trypanosomes. In the laboratory setting, cell wounding is typically induced using mechanical means to tear the cell membrane, such as using a microneedle to penetrate the plasma membrane or by scratching a culture dish to sever a portion of a cell.

For large disruptions, such as >1 µm tears in the membrane, a rapid resealing response is required to repair the membrane and maintain cell viability. Initially thought to be a passive process, resealing is now recognized to be an energy and calcium dependent process, resulting in calcium dependent exocytotic vesicle-vesicle and plasma membrane-vesicle fusions that patch the membrane tear. The vesicles sacrificed to provide the membrane patch are now known to be lysosomes. Internal lysosomal membrane is thus added to the cell surface to seal the disruption site. See McNeil, P. L. (2002) *J. Cell Sci.* 115(5):873; Togo, T., et al. (1999) *J. Cell Sci.* 112: 719; McNeil, P. L., and R. A. Steinhardt (2003) *Ann. Rev. Cell Dev. Biol.* 19:697.

The repair process appears to require actin depolymerization in order to allow access of the lysosomes to the plasma membrane. In addition, myosin and/or kinesin mediated contractile processes are thought to be involved in bringing the lysosomes into the proximity of the tear. In addition, it is known that subsequent resealing events occur more rapidly than the initial response to the wound, presumably by the increased production of lysosomes from the Golgi. Thus resealing of large disruptions is dependent on functional actin and the Golgi complex to facilitate assess of lysosomes to the wound site, and to reestablish stores of lysosomes to participate in the repair process.

Thus, although cell membrane wounding and subsequent repair is known in the art, there is no teaching or suggestion of inducing cell membrane wounding as a research tool or a therapeutic approach, for example, to permeabilize cells to active agents, or to kill malignant cells. Further, the possibility of using an agent that binds to a cell surface antigen to induce cell membrane wounding has not been suggested. Finally, there is no suggestion of inducing cell membrane wounding using an antibody to treat a disease or disorder in a human or animal patient.

SUMMARY OF THE INVENTION

Accordingly, it is a primary object of the invention to address the aforementioned need in the art by providing methods and compositions utilizing antibody induced cell membrane wounding to treat diseases or disorders in human or animal patients.

It is another object of the invention to provide improved compositions and methods for inducing cell membrane wounding, utilizing polyvalent agents to permeabilize and/or kill cells.

It is another object of the invention to provide improved compositions and methods for crosslinking an antibody or other polyvalent agent to provide enhanced cell membrane wounding and/or killing of cells.

It is an additional object of the invention to provide improved compositions and methods for treating diseases and disorders in human or animal patients mediated by cellular hyperproliferation or hyperactivity.

Accordingly, in one embodiment of the invention, a composition for inducing cell membrane wounding is provided, wherein said composition comprises a polyvalent agent that binds to a highly expressed cell surface antigen present on the surface of a cell. Preferably, the cell surface antigen is associated with the cytoskeleton of the cell.

In an additional embodiment, a composition is provided for permeabilizing a cell, comprising a polyvalent agent that binds to a highly expressed cell surface antigen present on the surface of a cell. In another aspect, a method for permeabilizing a cell is provided, comprising contacting a cell with a polyvalent agent that binds to a highly expressed cell surface antigen present on the surface of the cell.

In another embodiment, the cell membrane wounding is not survivable, in part at least by providing the polyvalent agent in an amount sufficient to continue to wound the cell such that the cell fails to or can no longer repair the wound.

Accordingly, the composition for inducing cell membrane wounding can also function as a composition for killing a cell. In addition, the composition for killing a cell is also useful in a method of killing a cell. Preferably, the cell is malignant, and is associated with a neoplasm of a body tissue such as, for example, nerve, lymphoid, ovarian, cervical, endometrial, testicular, prostate, kidney, colon, pancreas, stomach, intestinal, esophagus, lung, thyroid, adrenal, liver, bone, skin, mouth, throat, and the like. In an additional embodiment, the cell is hyperactive, and the hyperactivity of the cell mediates a disease or disorder that can be treated by the compositions and methods disclosed herein for killing the hyperactive cell.

In a particular embodiment, a method of treating a human patient suffering from a condition characterized by hyperproliferation of cells is provided, comprising administering an polyvalent agent that binds a highly expressed cell surface receptor on the surface of the hyperproliferating cells, wherein said polyvalent agent is administered in an amount effective to preferentially kill the hyperproliferating cells relative to normal cells. Preferably, the hyperproliferating cells are cancer cells. In another embodiment, the hyperproliferating cells are stimulated into a hyperproliferating condition by growth factors, cytokines, viral infection, and the like.

In a preferred embodiment, the amount of polyvalent agent effective to preferentially kill hyperproliferating cells is an amount that is at least sufficient to saturate the cell surface receptors of the hyperproliferating cells. In a more preferred embodiment, the amount of polyvalent agent effective to preferentially kill hyperproliferating cells is sufficient to saturate the cell surface receptors of normal cells possessing the highly expressed cell surface antigen, while maintaining viability of the normal cells within acceptable ranges for the health of the patient. Preferential killing of hyperproliferating cells relative to normal cells generally is achieved by providing an amount of polyvalent agent sufficient to reduce the viability of the hyperproliferating cells while not being sufficient to reduce the viability of normal cells to the same extent. For example, utilizing a cell membrane wounding antibody, the viability of neoplastic cells can be reduced by an amount that is at least ten percent greater, more preferably twenty percent greater, and even more preferably, thirty percent greater or more, relative to the viability of normal cells, even when both the neoplastic cells and the normal cells express the same cell surface antigen on their respective surfaces.

Accordingly, in one embodiment, there is provided a method of killing cancer cells, comprising contacting the cancer cells with a cytotoxic amount of an antibody inducing cell membrane wounding to the cancer cells. The cell membrane wounding cytotoxicity is distinct from complement mediated cytotoxicity or cellular mediated cytotoxicity. In an additional embodiment, the cell membrane wounding antibody is cytotoxic to cancer cells by a cell membrane wounding mechanism as well as a complement and/or cellular mediated cytotoxicity mechanism.

Preferably, the polyvalent agent is administered in an amount effective to kill rapidly dividing cells, such as neoplastic cells, but not to kill normal cells. In another embodiment, the polyvalent agent is administered in an amount effective to kill hyperproliferating cells, but not to kill cells exhibiting normal motility or normal adhesion properties.

In certain preferred embodiments, the method further comprises administering a cytotoxic agent in combination with the polyvalent agent that binds a highly expressed cell surface receptor on the surface of the hyperproliferating cells. The cytotoxic agent can be a chemotherapeutic agent, a radioactive isotope, a cytotoxic antibody, an immunoconjugate, a ligand conjugate, an immunosuppressant, a cell growth regulator and/or inhibitor, a toxin, or mixtures thereof.

In an additional embodiment, the method further comprises administering a crosslinking agent providing crosslinking of the cell membrane wounding antibody. Preferably the crosslinking agent is an antibody, such as an anti-kappa antibody, an anti-lambda antibody, an anti-mu antibody, or the like.

In a particular embodiment, the cancer cell is a neoplastic B cell, and the cell membrane wounding antibody is a VH4-34 antibody. In certain embodiments, the cell membrane wounding antibody is a VH4-34 antibody and the crosslinking agent is an anti-VH4-34 antibody that does not prevent binding of the VH4-34 antibody to the cell surface antigen on the B cell.

In another embodiment, a method for inducing cell membrane wounding is provided, comprising contacting a cell with a polyvalent agent that binds to a highly expressed cell surface antigen present on the surface of the cell, wherein the cell is a lymphoid cell. In certain embodiments, the polyvalent agent is an antibody, and the lymphoid cell is a B cell expressing the CDIM epitope. Preferably, the antibody is administered in an amount effective to preferentially wound hyperproliferating B cells relative to normal B cells. In an additional embodiment, the antibody is administered in an amount effective to wound hyperproliferating B cells but not to kill them.

In a particular embodiment, the method comprises (1) sampling the blood of a patient in need of treatment to determine the number of hyperproliferating B cells in the blood of the patient, (2) determining the susceptibility of the hyperproliferating B cells and normal B cells to wounding by the antibody, and (3) administering an amount of the antibody to the patient sufficient to preferentially wound and/or kill hyperproliferating B cells in the patient. The method can further comprise titrating in additional amounts of antibody to the patient to achieve the desired amount of cell wounding and/or killing.

In an additional embodiment, the method comprises (1) sampling the blood of a patient in need of treatment to determine the number of hyperproliferating B cells in the blood of the patient, (2) determining the susceptibility of the hyperproliferating B cells to wounding by the antibody, and (3) administering an amount of the antibody to the patient sufficient to wound hyperproliferating B cells in the patient. The method can further comprise administering an effective amount of a cytotoxic agent to the patient to achieve a desired reduction in number of hyperproliferating B cells in the patient.

In other embodiments, methods for inducing cell membrane wounding are provided, comprising contacting a cell with a polyvalent agent that binds to a highly expressed cell surface antigen on the surface of the cell, wherein the cell can be any cell expressing a highly expressed cell surface antigen. Thus, the cell can be a different cell type from a lymphoid cell, or can be a cell type other than a B cell. In another embodiment, the highly expressed cell surface antigen is not the CDIM epitope.

In an additional embodiment, a composition is provided for inducing cell membrane wounding, comprising a polyvalent agent that binds to a highly expressed cell surface antigen, wherein the composition for inducing cell membrane wounding can further comprise a crosslinking agent that augments the cytotoxicity of the polyvalent agent relative to the cytotoxicity of the polyvalent agent in the absence of the crosslinking agent.

In a particular embodiment, the polyvalent agent is an antibody, preferably an IgM. In another particular embodiment, the crosslinking agent is an antibody which binds IgM, providing crosslinking of the IgM bound to the surface of the cell.

In another embodiment a method for inducing cell membrane wounding is provided, comprising contacting a cell with a polyvalent agent that binds to a highly expressed cell surface antigen on the surface of the cell. The method can further comprise contacting the cell with a crosslinking agent that augments the cytotoxicity of the polyvalent agent relative to the cytotoxicity of the polyvalent agent in the absence of the crosslinking agent. In a preferred embodiment, the polyvalent agent is an antibody, preferably an IgM antibody, and the crosslinking agent is an antibody, preferably an antibody that binds IgM, providing crosslinking of the antibody bound to the surface of the cell. Preferably, the cell is a B cell and the antibody is an IgM with binding specificity for a CDIM epitope on the surface of the B cell. Preferably, the antibody is an anti-CDIM antibody and the crosslinking agent binds to the anti-CDIM antibody, providing crosslinking of the anti-CDIM antibody bound to the surface of the B cell. The crosslinking agent is preferably an anti-kappa or anti-lambda antibody or an anti-VH4-34 antibody.

Accordingly, a method of purging the bone marrow of malignant B cells from a patient in need thereof is provided, comprising contacting the bone marrow cells with an antibody having specific binding for a CDIM epitope on the surface of the B cells. The method can further comprise contacting the B cells with a crosslinking agent that crosslinks the antibody bound to the CDIM epitope on the surface of the B cells, thereby providing an enhanced cytotoxicity for the anti-CDIM antibody toward the malignant B cells. In a preferred embodiment, the method further comprises contacting the cells with a cytotoxic agent to further purge the bone marrow of malignant B cells.

In another embodiment, a composition is provided for killing hyperproliferating cells, comprising a polyvalent agent that binds to a highly expressed cell surface antigen present on the surface of a cell, wherein said polyvalent agent comprises crosslinking means providing a crosslinked polyvalent agent bound to the surface of the cell. The crosslinked polyvalent agent provides an enhanced killing of the hyperproliferating cells compared with the polyvalent agent in the absence of said crosslinking means.

In another embodiment, a pharmaceutical composition for treating a mammal suffering from a condition characterized by hyperproliferation of cells is provided, said pharmaceutical composition comprising a polyvalent agent that binds to a highly expressed cell surface antigen present on the surface of a cell. The pharmaceutical composition can further comprise a cytotoxic agent. Preferably, the composition further comprises crosslinking means that augment the cytotoxicity of the polyvalent agent. Preferably, the polyvalent agent kills hyperproliferating cells by inducing cell membrane wounding that the cell cannot repair.

In a particular embodiment, the crosslinking means can be a monofunctional crosslinking agent covalently bound to the polyvalent agent that binds to the highly expressed cell surface antigen on the cell. The crosslinking agent can comprise a crosslinking functionality such as a succinimide, maleimide or thiol or the like at the distal end of the crosslinking agent to crosslink with an adjacent polyvalent agent bound to the highly expressed cell surface antigen on the surface of the cell. Preferably the polyvalent agent is an antibody, such as a natural antibody, including IgM, IgG, IgA, IgD, IgE; a recombinant antibody, a monoclonal antibody, a polyclonal antibody, a chimeric antibody, a synthetic antibody such as a tetravalent antibody or fusion protein comprising an antibody; an antibody fragment such as Fab2, scFv, and the like. In a preferred embodiment the antibody is an IgM.

In an additional embodiment, the crosslinking means can be a crosslinking agent that binds to an antibody. In a preferred embodiment, the crosslinking means is an anti-kappa or anti-lambda agent that crosslinks adjacent antibodies bound to the highly expressed cell surface antigen on the surface of the cell.

In yet another embodiment, the crosslinking means can be a hydrophilic polymer or network of polymers, having a molecular weight of from about 100 to about 10,000 daltons, bearing a plurality of polyvalent agents with specific binding for the highly expressed cell surface antigen on the surface of the cell, such as antibodies, or portions of antibodies, e.g., Fab, or scFv.

The polyvalent agent that binds to the highly expressed cell surface antigen preferably binds with high affinity. Typically, the high affinity binding is at least $10^6$ $M^{-1}$, and preferably is between about $10^6$ $M^{-1}$ and about $10^8$ $M^{-1}$.

In an additional embodiment, a pharmaceutical composition is provided for treating a mammal suffering from a condition characterized by hyperproliferation of cells, comprising a polyvalent agent that binds to a highly expressed cell surface antigen present on the surface of a cell, wherein said polyvalent agent comprises a plurality of binding sites for the cell surface antigen on the surface of the cell. Preferably, the plurality of binding sites is at least five, and more preferably is from about 5 to about 100. In particular embodiments, the plurality of binding sites can be from about 5 to about 15, from about 15 to about 25, or from about 15 to about 50.

Preferably, the polyvalent agent comprising a plurality of binding sites for the cell surface antigen provides an augmented cytotoxicity of the hyperproliferating cells that is associated with a greater number of binding sites.

Additional objects, advantages and novel features of the invention will be set forth in part in the description which follows, and in part will become apparent to those skilled in the art upon examination of the following, or may be learned by practice of the invention.

BRIEF DESCRIPTION OF THE DRAWINGS

FIG. 1 illustrates that VH 4-34 encoded antibodies bind primary B cell lymphomas and leukemias.

FIG. 2 illustrates that VH4-34 encoded monoclonal antibodies bind and kill human B cell lines.

FIG. 4 illustrates that the killing of B cells by mAb 216 and vincristine is synergistic.

FIG. 6A illustrates the viability of cells treated with two VH4-34 antibodies in medium with and without calcium.

FIG. 6B illustrates the viability of cells treated with cytotoxic agents.

DETAILED DESCRIPTION OF THE INVENTION

I. Definitions and Overview

Figure 3:
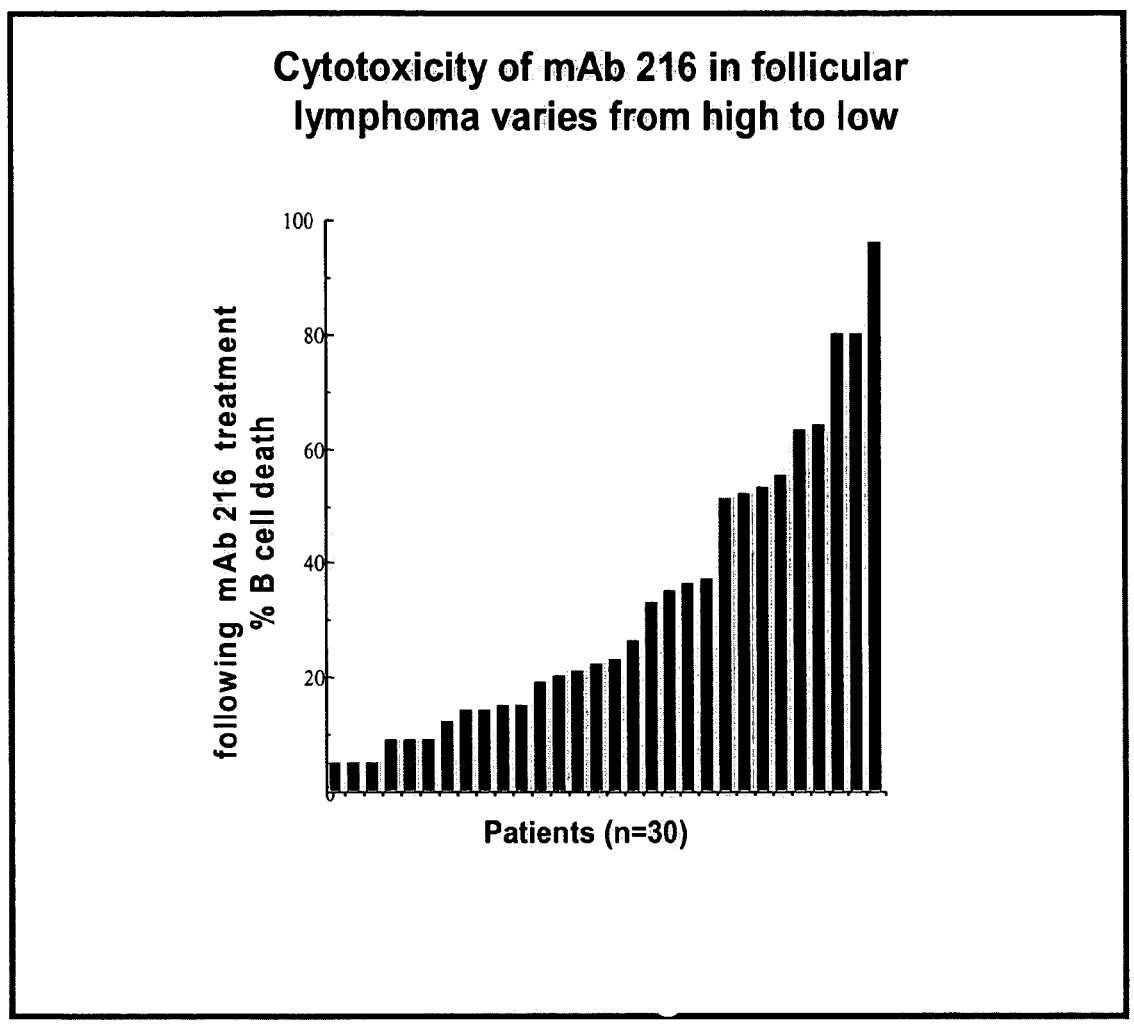
FIG. 3 illustrates the variability of the cytotoxicity of mAb 216 to follicular lymphoma cells.

Before the present invention is described in detail, it is to be understood that unless otherwise indicated this invention is not limited to particular buffers, excipients, chemotherapeutic agents, or the like, as such may vary. It is also to be understood that the terminology used herein is for the purpose of describing particular embodiments only and is not intended to limit the scope of the present invention.

It must be noted that as used herein and in the claims, the singular forms "a," "and" and "the" include plural referents unless the context clearly dictates otherwise. Thus, for example, reference to "a chemotherapeutic agent" includes two or more chemotherapeutic agents; reference to "a pharmaceutical excipient" includes two or more pharmaceutical excipients, and so forth.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

The terms "anti-CDIM antibody" and "CDIM binding antibody" as used herein refers to an antibody having specific binding for CDIM epitopes on a B cell. These terms will be used interchangeably herein.

The term "anti-VH4-34 antibody" refers to an antibody that specifically binds to an epitope present on the variable region of an antibody encoded by the VH4-34 gene, a VH4-34 antibody, and as such can include the germline sequence of the so called hypervariable regions or "complementarity determining regions" ("CDRs") of the VH4-34 antibody. However, the epitope is not a marker of a unique immunoglobulin formed by somatic hypermutation, such as a nongermline CDR. In a preferred embodiment, the epitope is present in the framework region of the antibody, and preferably does not include the CDR of the antibody. In an additional preferred embodiment, the anti-VH4-34 antibody does not interfere with the specific binding of the VH4-34 antibody to its antigen.

The term "9G4" refers to the rat monoclonal antibody that has been shown to recognize VH4-34 Ab (Stevenson, et al. *Blood* 68: 430 (1986)). The VH4-34 epitope identified by mAb 9G4 is conformation restricted and dependent on a unique sequence near amino acids 23-25 in the framework 1 region ("FR1") of the variable heavy chain. 9G4 is a species of anti-VH4-34 antibody.

The term "antibody" is used in the broadest sense and specifically covers intact natural antibodies, monoclonal antibodies, polyclonal antibodies, multispecific antibodies (e.g. bispecific antibodies) formed from at least two intact antibodies, synthetic antibodies such as tetravalent antibodies, and antibody fragments, so long as they exhibit the desired biological activity. Human antibodies include antibodies made in nonhuman species. The term antibody also encompasses Ig molecules formed only from heavy chains, such as those obtained from Camelids, and described in U.S. Pat. Nos. 6,765,087 and 6,015,695 to Casterman, for example. The term antibody also encompasses fusion or chemical coupling (i.e., conjugation) of antibodies with cytotoxic or cell regulating agents.

"Antibody fragments" comprise a portion of an intact antibody, preferably the antigen binding or variable region of the intact antibody. Examples of antibody fragments include Fab, Fab', F(ab')$_2$, and Fv fragments; diabodies; linear antibodies (Zapata, et al. (1995) *Protein Eng.* 8(10), 1057-1062) single-chain antibody molecules; and multispecific antibodies formed from antibody fragments.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., *Nature* 256, 495 (1975), or may be made by recombinant DNA methods (see, e.g., U.S. Pat. No. 4,816,567). The "monoclonal antibodies" can also be isolated from phage antibody libraries using the techniques described in Clackson et al. (1991) Nature, 352, 624-628 and Marks et al., (1991) *J. Mol. Biol.* 222, 581-597, for example.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., (1984) *Proc. Natl. Acad. Sci. USA,* 81, 6851-6855).

"Humanized" forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. For the most part, humanized antibodies are human immunoglobulins (recipient antibody) in which residues from a complementarity determining region (CDR) of the recipient are replaced by residues from a CDR of a non-human species (donor antibody) such as mouse, rat or rabbit having the desired specificity, affinity, and capacity. In some instances, framework region (FR) residues of the human immunoglobulin are replaced by corresponding non-human residues. Furthermore, humanized antibodies may comprise residues which are found neither in the recipient antibody nor in the imported CDR or framework sequences. These modifications are made to further refine and maximize antibody performance. In general, the humanized antibody will comprise substantially all of at least one, and typically two, variable domains, in which all or substantially all of the CDRs correspond to those of a non-human immunoglobulin and all or substantially all of the FRs are those of a human immunoglobulin sequence. The humanized antibody optimally also will comprise at least a portion of an immunoglobulin constant region (Fc), typically that of a human immunoglobulin. For further details, see Jones et al., (1986) *Nature* 321, 522-525; Reichmann et al., (1988) *Nature* 332, 323-329; and Presta (1992) *Curr. Op. Struct. Biol.* 2, 593-596. The humanized antibody includes a PRIMATIZED™ antibody wherein the antigen-binding region of the antibody is derived from an antibody produced by immunizing macaque monkeys with the antigen of interest.

"Single-chain Fv" or "scFv" antibody fragments comprise the VH and VL domains of antibody, wherein these domains are present in a single polypeptide chain. Preferably, the Fv polypeptide further comprises a polypeptide linker between the VH and VL domains which enables the scFv to form the desired structure for antigen binding. For a review of scFv see Pluckthun in *The Pharmacology of Monoclonal Antibodies*, vol. 113, Rosenburg and Moore eds., Springer-Verlag, New York, pp. 269-315 (1994).

The term "diabodies" refers to small antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al. (1993) *Proc. Natl. Acad. Sci. USA* 90, 6444-6448.

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

An agent which "arrests the growth of" or a "growth inhibitory agent" as used herein refers to a compound or composition which inhibits growth or proliferation of a cell, especially a neoplastic cell type expressing a B cell antigen such as the CD20 antigen as required. Thus, the growth inhibitory agent is one which for example, significantly reduces the percentage of neoplastic cells in S phase.

The terms "cancer" and "cancerous" refer to or describe the physiological condition in mammals that is typically characterized by unregulated cell growth.

The "CD20" antigen is a 35 kDa, non-glycosylated phosphoprotein found on the surface of greater than 90% of B cells from peripheral blood or lymphoid organs. CD20 is expressed during early pre-B cell development and remains until plasma cell differentiation. CD20 is present on both normal B cells as well as malignant B-cells. Other names for CD20 in the literature include "B-lymphocyte-restricted antigen" and "Bp35." The CD20 antigen is described in Clark et al. PNAS (USA) 82:1766 (1985), for example.

The term "cell wounding" refers to a survivable plasma membrane disruption event marked by the uptake into the cytosol of a normally membrane impermeant tracer. Cell wounding disruptions typically are in the range of between about 1 and 1000 µm$^2$, and thus are far larger than the membrane disruptions accompanying complement mediated cytotoxicity or perforin or even large pores formed by toxins or pore forming agents such as gramicidin or *Staphylococcus aureus* alpha toxin. Cell wounding is detected by the cellular repair mechanism manifested as a result of the wound, namely the expression of Lamp-1 on the cellular surface as a result of lysosomal fusion to repair the wound.

The term "cell wounding antibody" or "cell membrane wounding antibody" refers to an antibody, that upon binding to a highly expressed cell surface antigen, causes a survivable plasma membrane disruption event marked by the uptake into the cytosol of a normally membrane impermeant tracer. Cell wounding antibodies elicit the cellular repair mechanism manifested as a result of the wound, namely the expression of Lamp-1 on the cellular surface as a result of lysosomal fusion to repair the wound.

The term "chemotherapeutic agent" refers to a chemical compound useful in the treatment of cancer or other condition characterized by a hyperproliferation of cells.

The terms "cytotoxic agent" and "cytotoxin" as used herein refer to a substance that inhibits or arrests the growth of, inhibits or prevents the function of cells, and/or causes death of cells. The term is intended to include one or more radioactive isotopes, chemotherapeutic agents, immunosuppressants, cell growth regulators and/or inhibitors, which can be small molecule therapeutics, cytotoxic antibodies, and toxins such as enzymatically active toxins of bacterial, fungal, plant or animal origin, or fragments thereof. The term also includes immunoconjugates comprising antibodies labeled with toxins or radioactive isotopes for specific binding to a target cell, as well as other ligand conjugates, such as radiolabeled ligands, and toxin-labeled ligands. In addition, one or more cytotoxic agents can be used in combination.

A "disorder" is any condition that would benefit from treatment with the combination therapy described herein. This includes chronic and acute disorders or diseases including those pathological conditions which predispose the mammal to the disorder in question. Non-limiting examples of disorders to be treated herein include cancer, hematological malignancies, leukemias and lymphoid malignancies and autoimmune diseases such as inflammatory and immunologic disorders.

The term "highly expressed cell surface antigen" refers to a surface antigen accessible on the surface of the cell (i.e., that does not require cell permeabilization to exhibit binding) that is present in at least 10$^4$ copies per cell, or that is present on at least a portion of the cell at a density of at least 25 copies/µm$^2$. Cell surface antigens include cell surface expressed molecules such as receptors, immunoglobulins, cytokines, glycoproteins, etc.

The terms "hyperproliferation" and "hyperproliferating" refer to the abnormal growth of a cell type, which can be cancerous or benign. Generally, hyperproliferating cells exhibit a rate of cell division that is at least about ten percent greater than the rate of cell division exhibited by normal cells of that cell type. Hyperproliferation includes the polyclonal expansion of B cells secreting autoantibodies that mediate autoimmune diseases.

The term "immunoconjugates" refers to antibodies conjugated to cytotoxic agents, which can be covalent or noncovalently associated.

The term "intravenous infusion" refers to introduction of an agent into the vein of an animal or human patient over a period of time, generally greater than approximately 15 minutes, and more generally between approximately 30 to 90 minutes.

The term "intravenous bolus" or "intravenous push" refers to drug administration into a vein of an animal or human such that the body receives the drug in approximately 15 minutes or less, generally 5 minutes or less.

The term "mammal" for purposes of treatment refers to any mammalian species, including humans, domestic and farm animals, and zoo, sports, pet or wild animals. When the cell surface antigen is the CDIM antigen, the CDIM antigen expression should not be expressed on erythrocytes of the mammalian species if hemagglutination is to be avoided. Preferably, the CDIM antigen is predominantly restricted to cells of B cell lineage after birth.

The humanized anti-CD20 antibody referred to as the "RITUXAN® brand" anti-CD20 antibody is a genetically engineered chimeric murine/human monoclonal antibody directed against the CD20 antigen. Rituximab is the antibody called "C2B8" in U.S. Pat. No. 5,736,137 issued Apr. 7, 1998. The RITUXAN® brand of C2B8 antibody is indicated for the treatment of patients with relapsed or refractory low-grade or follicular, CD20 positive, B cell non-Hodgkin's lymphoma.

The term "specific binding" refers the property of having a high binding affinity of at least $10^6$ $M^{-1}$, and usually between about $10^6$ $M^{-1}$ and about $10^8$ $M^{-1}$.

The term "subcutaneous administration" refers to introduction of an agent under the skin of an animal or human patient, preferable within a pocket between the skin and underlying tissue, by relatively slow, sustained delivery from a drug receptacle. The pocket may be created by pinching or drawing the skin up and away from underlying tissue.

The term "subcutaneous bolus" refers to drug administration beneath the skin of an animal or human patient, where bolus drug delivery is preferably less than approximately 15 minutes, more preferably less than 5 minutes, and most preferably less than 60 seconds. Administration is preferably within a pocket between the skin and underlying tissue.

The term "subcutaneous infusion" refers to introduction of a drug under the skin of an animal or human patient, preferably within a pocket between the skin and underlying tissue, by relatively slow, sustained delivery from a drug receptacle for a period of time including, but not limited to, 30 minutes or less, or 90 minutes or less. Optionally, the infusion may be made by subcutaneous implantation of a drug delivery pump implanted under the skin of the animal or human patient, wherein the pump delivers a predetermined amount of drug for a predetermined period of time, such as 30 minutes, 90 minutes, or a time period spanning the length of the treatment regimen.

The term "therapeutically effective amount" is used to refer to an amount of an active agent having a growth arrest effect or causes the death of the cell. In certain embodiments, the therapeutically effective amount has the property of permeabilizing cells, inhibiting proliferative signaling, inhibiting cellular metabolism, promoting apoptotic activity, or inducing cell death. In particular aspects, the therapeutically effective amount refers to a target serum concentration that has been shown to be effective in, for example, slowing disease progression. Efficacy can be measured in conventional ways, depending on the condition to be treated. For example, in lymphoid cancers, efficacy can be measured by assessing the time to disease progression (TTP), or determining the response rates (RR).

The terms "treat," "treatment" and "therapy" and the like as used within the context of the present invention, are meant to include therapeutic as well as prophylactic, or suppressive measures for a disease or disorder leading to any clinically desirable or beneficial effect, including but not limited to alleviation of one or more symptoms, regression, slowing or cessation of progression of the disease or disorder. Thus, for example, the term treatment includes the administration of an agent prior to or following the onset of a symptom of a disease or disorder thereby preventing or removing all signs of the disease or disorder. As another example, the term includes the administration of an agent after clinical manifestation of the disease to combat the symptoms of the disease. Further, administration of an agent after onset and after clinical symptoms have developed where administration affects clinical parameters of the disease or disorder, such as the degree of tissue injury or the amount or extent of metastasis, whether or not the treatment leads to amelioration of the disease, comprises "treatment" or "therapy" within the context of the invention.

II. Cell Membrane Wounding Antibodies

The VH4-34 antibodies (variable heavy region) are one of the 53 identified human functional antibody germline antibodies, encoded by germline genes (VH4.21). Cook, G. P., et al., (1994) *Nat. Genet.* 7, 162-168. The gene for VH4-34 antibodies is present in all haplotypes and no sequence variation has been reported in germline DNA isolated from unrelated individuals. Weng, N. P., et al., (1992) *Eur. J. Immunol.* 22, 1075-1082; van der Maarel, S., et al., (1993) *J. Immunol.* 150, 2858-2868. Antibodies encoded by the VH4-34 gene have been shown to possess unique properties. All mAbs directed against the "I" or "i" antigens of red blood cells (RBCs) are encoded by the VH4-34 gene, are generally of the IgM class, and are classically described as cold agglutinins (CAs) because they agglutinate RBCs at 4° C. Pascual, V., et al., (1991) *J. Immunol.* 146, 4385-4391; Pascual, V., (1992) *J. Immunol.* 149, 2337-2344; Silberstein, L. E., et al., (1991) *Blood* 78, 2372-2386. The ligands recognized by CAs are linear or branched glycoconjugates present on proteins and/or lipids of the RBCs. Newborn and cord blood RBC possess the linear i antigen. The branched I chain is generated after birth. Pruzanski, W. et al., (1984) *Clin. Immunol. Rev.* 3, 131-168; Roelcke, D. (1989) *Transfusion Med. Rev.* 2, 140-166. The "i" antigen recognized on human B cells is a linear lactosamine determinant that is sensitive to the enzyme endo-beta-galactosidase. Sequence analysis of independently derived VH4-34 anti-B cell/anti-i mAbs has shown that they are in germline configuration. Bhat N. M., et al., (1997) *Clin. Exp. Immunol.* 108, 151-159.

In vivo, the expression of VH4-34 gene derived antibodies is strictly regulated. Although 4-8% of human B cells express VH4-34 encoded antibody, serum levels of VH4-34 derived antibodies are negligible in normal adults. Stevenson F. K., et al., (1989) *Br. J. Haematol.* 72, 9-15; Kraj P, et al., (1995) *J. Immunol.* 154, 6406-6420. Increase in circulating VH4-34 derived antibodies is seen only in selective pathological conditions including viral infections (Epstein Barr (mononucleosis), human immunodeficiency virus and hepatitis C virus), *Mycoplasma pneumoniae* and certain autoimmune diseases. See also Bhat, N. M., et al. (2005) *Human Antibodies* 13, 63-68.

The present inventors have extensively studied VH4-34 encoded antibodies and their role in autoimmune disorders. Previous studies demonstrated that certain anti-B cell VH4-34 antibodies are cytotoxic to B cells and lead to decreased B cell proliferation Bhat, N. et al. (1997) *Clin. Exp. Immunol.* 108:151; Bhat, N., et al., (2001) *Crit. Rev. Oncol. Hematol.* 39, 59. Cytotoxicity was shown to be independent of complement, and to be highly temperature dependent, resulting in greater cell death and the formation of plasma membrane defects such as blebs and pores on the cell surface when treated at 4° C. The plasma membrane defects were shown to be significantly larger than the pores formed by other well known pore-forming proteins, such as C9 complement component (~100 Å) and perforin (~160 Å). It was suggested that the cytotoxicity may be mediated by a novel mechanism.

The present inventors have made the surprising and unexpected discovery that these VH4-34 gene derived antibodies can induce cell membrane wounding in B cells, which is distinct from the large plasma membrane defects observed in cells killed by anti-CDIM antibodies reported previously (Bhat, N. et al. (1997) *Clin. Exp. Immunol.* 108:151; Bhat, N., et al., (2001) *Crit. Rev. Oncol. Hematol.* 39, 59). Although the antibody causes pores and membrane defects in cells under certain conditions, when treated at sublethal concentrations, some of the B cells are merely wounded, and are capable of repairing the wound in some cases. Although membrane injury is a common threat faced by nucleated mammalian cells, the fact that an antibody could be the direct cause of membrane injury is novel.

Further, the present inventors have demonstrated that antibody induced cell membrane wounding is repaired in a manner similar to any other membrane wound. Cells treated with these complement independent cytotoxic antibodies attempt to repair the antibody induced cell membrane wound utilizing lysosomal fusion with the plasma membrane to patch the membrane wound, resulting in the appearance of lysosomal membrane proteins on the cell surface. It is also demonstrated that when the cells are unable to repair the damage, death ultimately results.

In addition, the present inventors have discovered that the wounded cells are permeabilized, at least transiently, and become more susceptible to the action of additional cytotoxic agents, providing novel treatment options having enhanced efficacy for treatment of human and animal diseases and disorders. The cell membrane wound results in permeabilization of the B cells and allows entry of cytotoxic agents such as chemotherapeutic agents, thus increasing the efficacy of the chemotherapeutic agents, even in cells that are resistant or impermeable to such agents, or in cells that actively transport them out of the cell.

Because the mechanism of cell death and wounding provided by the CDIM binding antibodies is different from the cytotoxic mechanism utilized by conventional cytotoxic antibodies (complement or cell mediated killing), the combination of the CDIM binding antibodies with conventional immunotherapies can provide an enhanced efficiency of killing by cytotoxic antibodies binding additional B cell antigens, especially under conditions of immunodeficiencies such as complement depletion or deficiency.

Further, the action of the cell wounding antibodies can be enhanced by the addition of a crosslinking agent that augments the cytotoxicity of the antibodies relative to the cytotoxicity of the antibodies in the absence of the crosslinking agent. This observation is distinguishable from the apoptosis induced by hypercrosslinking, for example, reported by Marches, R., et al. (1995) *Ther. Immunol.* 2, 125, stating that crosslinking of IgM and resultant signaling may be a major factor in inducing and maintaining dormancy and apoptosis after hypercrosslinking.

In a preferred embodiment, the antibodies according to one aspect of the invention are VH4-34 encoded monoclonal antibodies that bind the CDIM epitope on human B cells, such as described in Grillot-Courvalin, C., et al. (1992) *Eur. J. Immunol.* 22, 1781-1788; Bhat, N. M., et al. (1993) *J. Immunol.* 151, 5011-5021; Silberstein, L. E., et al. (1996) *Blood Cells, Molecules, and Diseases,* 22, 126-138, and as illustrated in FIGS. 1 and 2. These antibodies are cytotoxic to B cells obtained from relapsed follicular lymphoma patients, as illustrated in FIG. 3. In addition, the antibodies are cytotoxic to B cell lines, as shown in FIG. 4. In a preferred embodiment, these mAbs are produced by fusion of human lymphocytes and a heteromyeloma cell line, which produces a hybridoma secreting human antibody. For example, mAb 216 is a human IgM encoded by the VH4-34 gene, and is a preferred embodiment of the CDIM binding VH4-34 antibodies described herein. MAb 216 is further described in U.S. Pat. Nos. 5,593,676 and 5,417,972 and EP 712 307 B1 to Bhat, et al.

Additional VH4-34 derived antibodies that bind the CDIM epitope include RT-2B, FS 12, A6(H4C5), Cal-4G, S20A2, FS 3, Gee, HT, Z2D2, Y2K. Certain of these antibodies are characterized by a CDR3 sequence rich in basic amino acid residues, and by particularly strong binding when the net charge of the CDR3 is +2. Accordingly, any antibody possessing a net positive CDR, particularly CDR3, and exhibiting binding to the CDIM epitope, is encompassed within the scope of the invention and as claimed in the appended claims.

However, it will be appreciated by one skilled in the art that any antibody that binds the CDIM epitope and exhibits cytotoxicity to a B cell is encompassed within the scope of the CDIM binding antibodies described herein.

III. Methods and Compositions for Inducing Cell Membrane Wounding

Accordingly, in one embodiment of the invention, a composition for inducing cell membrane wounding is provided, wherein said composition comprises a polyvalent agent that binds to a highly expressed cell surface antigen present on the surface of a cell. Preferably, the cell surface antigen is associated with the cytoskeleton of the cell. For example, the cell surface antigen remains associated with the cell after removal of soluble components by detergent extraction. Cell membrane wounding is a survivable membrane injury repaired by lysosomal fusion, detectable by the appearance or expression of lysosomal proteins on the surface of the cell, and results in at least transient permeabilization of the cell.

In an additional embodiment, a composition is provided for permeabilizing a cell, comprising a polyvalent agent that binds to a highly expressed cell surface antigen present on the surface of a cell. In another aspect, a method for permeabilizing a cell is provided, comprising contacting a cell with a polyvalent agent that binds to a highly expressed cell surface antigen present on the surface of the cell.

In other embodiments, methods for inducing cell membrane wounding are provided, comprising contacting a cell with a polyvalent agent that binds to a highly expressed cell surface antigen on the surface of the cell, wherein the cell can be any cell expressing a highly expressed cell surface antigen. Thus, the cell can be a different cell type from a lymphoid cell, or can be a cell type other than a B cell. In another embodiment, the highly expressed cell surface antigen is not the CDIM epitope.

The methods and compositions described herein also encompass the use of a cell membrane wounding polyvalent agent, particularly a cell membrane wounding antibody, in the manufacture of a medicament for the treatment of a mammal suffering from a disease or disorder characterized by a hyperproliferation of cells.

IV. Methods and Compositions for Killing and/or Inhibiting the Growth of Cells In another embodiment, the cell membrane wounding is not survivable, in part at least by providing the polyvalent agent in an amount sufficient to continue to wound the cell such that the cell fails to or can no longer repair the wound. Cell wounding which is lethal can be achieved by providing the polyvalent agent in an amount in sufficient excess relative to the number of highly expressed cell surface antigens present on the surface of the cell, such that membrane repair is not effective or cannot be maintained. Cell wounding which is lethal can also be achieved by providing an agent that blocks or interferes with the repair mechanism, such as an anti-actin agent or agent that affects the association of the cell surface receptor with the underlying cytoskeleton of the cell. Cell wounding which is lethal can also be achieved by providing an agent that affects or interferes with cell adhesion and/or motility.

Accordingly, the composition for inducing cell membrane wounding can also function as a composition for killing a cell. In addition, the composition for killing a cell is also useful in a method of killing a cell. Preferably, the cell is malignant, and is associated with a neoplasm of a body tissue such as, for example, nerve, lymphoid, ovarian, cervical, endometrial, testicular, prostate, kidney, colon, pancreas, stomach, intestinal, esophagus, lung, thyroid, adrenal, liver, bone, skin, mouth, throat, and the like. In an additional embodiment, the cell is hyperactive, and the hyperactivity of the cell mediates a disease or disorder that can be treated by the compositions and methods disclosed herein for killing the hyperactive cell.

V. Administration of Additional Cytotoxic Agents

The present inventors have made the surprising discovery that the toxicity of these cell membrane wounding antibodies can be markedly and even synergistically enhanced by the addition of a cytotoxic agent, including chemotherapeutic agents, radioactive isotopes, cytotoxic antibodies, immunoconjugates, ligand conjugates, immunosuppressants, cell growth regulators and/or inhibitors, toxins, or mixtures thereof.

Accordingly, in certain preferred embodiments, the method further comprises administering a cytotoxic agent in combination with the polyvalent agent that binds a highly expressed cell surface receptor on the surface of the hyperproliferating cells. The cytotoxic agent can be a chemotherapeutic agent, a radioactive isotope, a cytotoxic antibody, an immunoconjugate, a ligand conjugate, an immunosuppressant, a cell growth regulator and/or inhibitor, a toxin, or mixtures thereof.

In addition, the cell membrane wounding can be utilized to permeabilize cells to allow access to the cytosol for normally impermeant agents, such as charged drugs, proteins and peptides, nucleic acids, gene therapy agents, or gene expression modifiers. In this manner, the cell membrane wounding can be used to modify cellular activities, gene expression, or responses to proliferative signaling, for example, in a cell, and provides a means for treating a patient suffering from a disease or disorder characterized by hyperproliferating cells or hyperactive cells, without actually having to kill the cells.

VI. Preferential Killing of Neoplastic Cells

In particular embodiments, a method of treating a human patient suffering from a condition characterized by hyperproliferation of cells is provided, comprising administering an polyvalent agent that binds a highly expressed cell surface receptor on the surface of the hyperproliferating cells, wherein said polyvalent agent is administered in an amount effective to preferentially kill the hyperproliferating cells relative to normal cells. Preferably, the hyperproliferating cells are cancer cells. In another embodiment, the hyperproliferating cells are stimulated into a hyperproliferating condition by growth factors, cytokines, viral infection, and the like.

In a preferred embodiment, the amount of polyvalent agent effective to preferentially kill hyperproliferating cells is an amount that is at least sufficient to saturate the cell surface receptors of the hyperproliferating cells. In a more preferred embodiment, the amount of polyvalent agent effective to preferentially kill hyperproliferating cells is sufficient to saturate the cell surface receptors of normal cells possessing the highly expressed cell surface antigen, while maintaining viability of the normal cells within acceptable ranges for the health of the patient. Preferential killing of hyperproliferating cells relative to normal cells generally is achieved by providing an amount of polyvalent agent sufficient to reduce the viability of the hyperproliferating cells while not being sufficient to reduce the viability of normal cells to the same extent. For example, utilizing a cell membrane wounding antibody, the viability of neoplastic cells can be reduced by an amount that is at least ten percent greater, more preferably twenty percent greater, and even more preferably, thirty percent greater or more, relative to the viability of normal cells, even when both the neoplastic cells and the normal cells express the same cell surface antigen on their respective surfaces.

Accordingly, in one embodiment, there is provided a method of killing cancer cells, comprising contacting the cancer cells with a cytotoxic amount of an antibody inducing cell membrane wounding to the cancer cells. The cell membrane wounding cytotoxicity is distinct from complement mediated cytotoxicity or cellular mediated cytotoxicity. In an additional embodiment, the cell membrane wounding antibody is cytotoxic to cancer cells by a cell membrane wounding mechanism as well as a complement and/or cellular mediated cytotoxicity mechanism.

Preferably, the polyvalent agent is administered in an amount effective to kill hyperproliferating cells, such as neoplastic cells, but not to kill nonneoplastic cells. In another embodiment, the polyvalent agent is administered in an amount effective to kill hyperproliferating cells, but not to kill cells exhibiting normal motility or normal adhesion properties.

Figure 8:
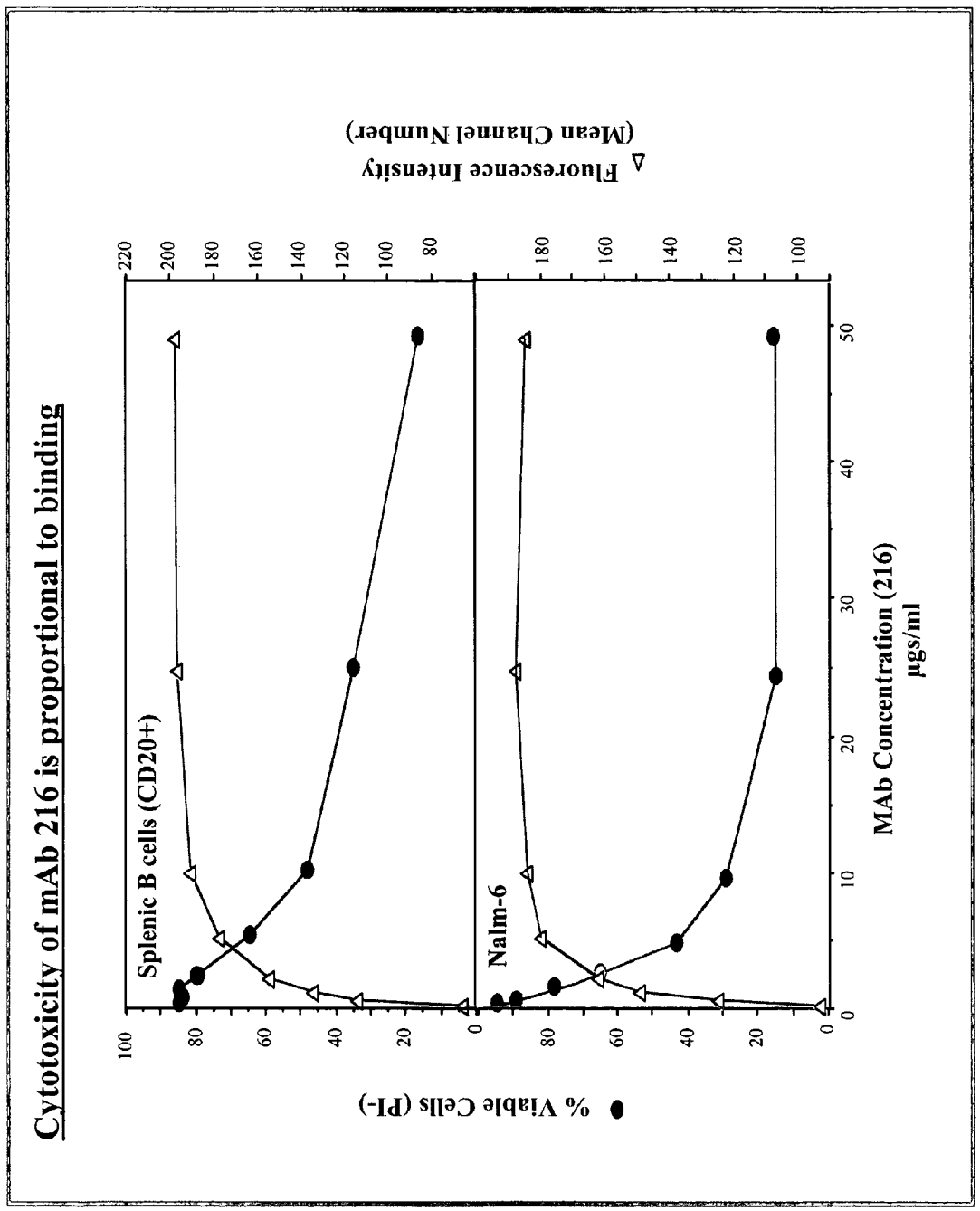
FIG. 8 illustrates the dose dependent cytotoxicity of an antibody that induces cell membrane wounding.

As discussed in Example 10, and shown in FIG. 8, the dependence of cell viability on the concentration of the polyvalent agent can vary significantly between the cell types. For example, in Example 10, at a concentration of approximately 5 μg/ml antibody, splenic B cells exhibited a viability of about 65%, while Nalm-6 cells at the same concentration of antibody exhibited a viability of only about 42%. This amount of antibody is sufficient to provide at least a three fold excess to the total amount of CDIM epitopes on the Nalm-6 cells, and is closer to a five fold excess for the splenic B cells. At a higher concentration of antibody, approximately 10 μg/ml, splenic B cells exhibited a viability of about 48%, while Nalm-6 cells exhibited a viability of only about 30%. Thus, the B cell lines exhibited greater susceptibility to killing with the CDIM binding antibody than normal B lymphocytes, suggesting that neoplastic B cells were more susceptible to killing with mAb 216 than normal B cells.

Without wishing to be bound by theory, it is hypothesized that the cessation of membrane traffic within the rapidly dividing cells interferes with or slows down the repair mechanism required to maintain cell viability in the wounded cells. Alternatively, there may be additional differences between the neoplastic B cells and mature B cells that cause the increased susceptibility, particularly in the association of the CDIM epitope with the underlying cytoskeleton of the B cell, or the differential expression or activity of adhesion molecules, and/or motility of the cells.

In another embodiment, a method for inducing cell membrane wounding is provided, comprising contacting a cell with a polyvalent agent that binds to a highly expressed cell surface antigen present on the surface of the cell, wherein the cell is a lymphoid cell. In certain embodiments, the polyvalent agent is an antibody, and the lymphoid cell is a B cell expressing the CDIM epitope. Preferably, the antibody is administered in an amount effective to preferentially wound hyperproliferating B cells relative to normal B cells. In a particular embodiment, the method comprises (1) sampling the blood of a patient in need of treatment to determine the number of hyperproliferating B cells in the blood of the patient, (2) determining the susceptibility of the hyperproliferating B cells and normal B cells to wounding by the antibody, and (3) administering an amount of the antibody to the patient sufficient to preferentially wound and/or kill hyperproliferating B cells in the patient. The method can further comprise titrating in additional amounts of antibody to the patient to achieve the desired amount of cell wounding and/or killing. The method can further comprise contacting the cells with a cytotoxic agent.

In an additional embodiment, the method comprises (1) sampling the blood of a patient in need of treatment to determine the number of hyperproliferating B cells in the blood of the patient, (2) determining the susceptibility of the hyperproliferating B cells to wounding by the antibody, and (3) administering an amount of the antibody to the patient sufficient to wound hyperproliferating B cells in the patient. The method can further comprise titrating in additional amounts of antibody to the patient to achieve the desired amount of cell wounding and/or killing. The method can further comprise contacting the cells with a cytotoxic agent.

VII. Methods and Compositions for Augmenting Cell Membrane Wounding

In an additional embodiment, a composition is provided for inducing cell membrane wounding, comprising a polyvalent agent that binds to a highly expressed cell surface antigen, wherein the composition for inducing cell membrane wounding can further comprise a crosslinking agent that augments the cytotoxicity of the polyvalent agent relative to the cytotoxicity of the polyvalent agent in the absence of the crosslinking agent.

In a particular embodiment, the polyvalent agent is an antibody, preferably an IgM. In another particular embodiment, the crosslinking agent is an antibody which binds IgM, providing crosslinking of the IgM bound to the surface of the cell, and further providing additional membrane wounding and cytotoxicity. In a preferred embodiment, the cell membrane wounding is augmented by the crosslinking agent. In certain preferred embodiments, the augmentation is at least about 25%, and more preferably is about 50% or more.

In another embodiment a method for inducing cell membrane wounding is provided, comprising contacting a cell with a polyvalent agent that binds to a highly expressed cell surface antigen on the surface of the cell, and further comprising contacting the cell with a crosslinking agent that augments the cytotoxicity of the polyvalent agent relative to the cytotoxicity of the polyvalent agent in the absence of the crosslinking agent. In a preferred embodiment, the polyvalent agent is an IgM, and the crosslinking agent is an antibody that binds IgM, providing crosslinking of the IgM bound to the surface of the cell. Preferably, the cell is a B cell and the antibody is an IgM with binding specificity for a CDIM epitope on the surface of the B cell. In one embodiment, the antibody is a VH4-34 antibody and the crosslinking agent is an anti-kappa antibody, anti-lambda antibody or anti-VH4-34 antibody.

Accordingly, a method of purging the bone marrow of malignant B cells from a patient in need thereof is provided, comprising contacting the bone marrow cells with an antibody having specific binding for a CDIM epitope on the surface of the B cells. The method can further comprise contacting the B cells with a crosslinking agent that crosslinks the antibody bound to the CDIM epitope on the surface of the B cells, thereby providing an enhanced cytotoxicity for the anti-CDIM antibody toward the malignant B cells. In a more preferred embodiment, the method further comprises contacting the cells with a cytotoxic agent to further purge the bone marrow of malignant B cells.

In another embodiment, a composition is provided for killing hyperproliferating cells, comprising a polyvalent agent that binds to a highly expressed cell surface antigen present on the surface of a cell, wherein said polyvalent agent comprises crosslinking means providing a crosslinked polyvalent agent bound to the surface of the cell. The crosslinked polyvalent agent provides an enhanced killing of the hyperproliferating cells compared with the polyvalent agent in the absence of said crosslinking means.

In another embodiment, a pharmaceutical composition for treating a mammal suffering from a condition characterized by hyperproliferation of cells is provided, said pharmaceutical composition comprising a polyvalent agent that binds to a highly expressed cell surface antigen present on the surface of a cell. Preferably, the composition further comprises crosslinking means that augment the cytotoxicity of the polyvalent agent. Preferably, the polyvalent agent kills hyperproliferating cells by inducing cell membrane wounding that the cell cannot repair.

In a particular embodiment the crosslinking means can be a functionalized agent covalently bound to the polyvalent agent that binds to the highly expressed cell surface antigen on the cell, and capable of crosslinking with an adjacent polyvalent agent bound to the cell. For example, a mono-, di or tri-functional crosslinking agent can be covalently attached to the polyvalent agent. The crosslinking agent can comprise a functionality such as a maleimide, succinimide, carbodiimide, or thiol, etc. at the distal end of the crosslinking agent to crosslink with an adjacent polyvalent agent bound to the highly expressed cell surface antigen on the surface of the cell. For example, U.S. Patent Application Publication No. 2004/0121951, incorporated by reference herein, describes numerous examples of crosslinking agents that can be used in the presently described compositions. One skilled in the art will recognize that there is no particular limitation to the crosslinking means that can be employed in the composition. Any crosslinking means can be utilized so long as the crosslinking agent has sufficient length to contact an adjacent polyvalent agent, and sufficient reactivity to link to the adjacent polyvalent agent.

Preferably the polyvalent agent is an antibody, such as a natural antibody, including IgM, IgG, IgA, IgD, IgE; a recombinant antibody or chimeric antibody; a monoclonal antibody; a polyclonal antibody; a synthetic antibody such as a tetravalent antibody, for example, as described in WO 02/096948, incorporated by reference herein, or fusion protein comprising an antibody; an antibody fragment such as Fab2, scFv, or the like. In a preferred embodiment the antibody is an IgM.

In an additional embodiment, the crosslinking means can be a crosslinking agent that binds to an antibody. In a preferred embodiment, the crosslinking means is an anti-kappa or anti-lambda or anti-mu agent that crosslinks adjacent antibodies bound to the highly expressed cell surface antigen on the surface of the cell. In an additional preferred embodiment, the polyvalent agent is a IgM antibody of the VH4-34 class of antibodies, such as mAb 216, RT-2B, FS 12, A6(H4C5), Cal-4G, S20A2, FS 3, Gee, HT, Z2D2, or Y2K, and the crosslinking agent is an anti-VH4-34 antibody binding antibody. Preferably, the anti-VH4-34 antibody does not prevent the binding of the VH4-34 antibody to the cell surface antigen. In a particular embodiment, the anti-VH4-34 antibody is 9G4.

In yet another embodiment, the crosslinking means can be a hydrophilic polymer or network of polymers, having a molecular weight of from about 100 to about 1,000,000 Daltons, or more preferably, from about 1000 to about 250,000 Daltons, bearing a plurality of polyvalent agents with specific binding for the highly expressed cell surface antigen on the surface of the cell. The hydrophilic polymer can be a polypeptide or a carbohydrate. Polypeptides can comprise basic amino acids bearing free amino groups to facilitate covalent attachment of the polyvalent agent to the polypeptide backbone, such as $(Ala)_n Lys$, where n can be from 2 to 20, for example. The covalently attached polyvalent agent can include antibody fragments, such as Fab', $Fab_2'$, or intact IgM, for example. Covalent attachment can be conveniently provided using difunctional crosslinking agents, such as disuccinimde or dimaleimide crosslinking agents, although any suitable means of attachment can be utilized.

The polyvalent agent that binds to the highly expressed cell surface antigen preferably exhibits specific binding, i.e., it binds with high affinity. Typically, the high affinity binding is at least $10^6 M^{-1}$, and typically is between about $10^6 M^{-1}$ and about $10^8 M^{-1}$.

In an additional embodiment, a pharmaceutical composition is provided for treating a mammal suffering from a condition characterized by hyperproliferation of cells, comprising a polyvalent agent that binds to a highly expressed cell surface antigen present on the surface of a cell, wherein said polyvalent agent comprises a plurality of binding sites for the cell surface antigen on the surface of the cell. Preferably, the plurality of binding sites is at least five, and more preferably is from about 5 to about 100. In particular embodiments, the plurality of binding sites can be from about 5 to about 15, from about 15 to about 25, or from about 15 to about 50, or more.

Preferably, the polyvalent agent comprising a plurality of binding sites for the cell surface antigen provides an augmented cytotoxicity of the hyperproliferating cells that is associated with a greater number of binding sites.

VIII. In Vivo Therapeutic Uses

The cell wounding antibody mAb 216 was tested in vivo in human patients, as described in detail in Example 12. Patients (adults diagnosed with ALL) were refractory to treatment with the standard regimen of chemotherapeutic drugs (VCR/DNR/ASPR/prednisone), i.e., blast counts no longer decreased in response to chemotherapeutic treatment, and patients were terminal. Antibody was administered in a dose of 1.25 mg/kg to two patients on days 0 and 7, as indicated by arrows in FIGS. 9A and 9B. Approximate serum antibody concentrations were 26 µg/ml and 25 µg/ml serum, respectively, based on patient weight, dosage and approximate serum volume (assuming 30% hematocrit). Blast counts in each patient (Patient 1 and Patient 2) were approximately $125 \times 10^6$/ml and $65 \times 10^6$/ml, respectively, at the time of mAb 216+VCR treatment. Relative to in vitro studies performed at concentrations of about $10^6$ cells/ml, these mAb concentrations correspond approximately to 0.2 µg/$10^6$ cells and 0.38 µg/$10^6$ cells, respectively, concentrations that are well below the lethal threshold concentrations demonstrated in vitro for mAb 216 killing of B cells.

In the absence of VCR, blast counts decreased transiently, a result likely due more to complement mediated cell killing than to mAb 216 mediated cell wounding at the low antibody concentration tested. However, in combination with VCR, a dramatic decrease in blast cell counts was observed, as demonstrated in FIGS. 9A and 9B, and resulted in extension of life for these patients. These data demonstrate the dramatically enhanced cell death of leukemic blasts due to the synergistic combination of mAb 216 and VCR in vivo. Even at very low concentrations (sublethal) concentrations of mAb 216, Where blasts were merely wounded or permeabilized by mAb 216 treatment, susceptibility of cells to VCR toxicity was markedly enhanced and treatment efficacy enhanced. Accordingly, these results represent a significant advance in cancer therapeutic efficacy.

IX. Kits

The polyvalent agents described herein, in particular, cell membrane wounding antibodies, can be used in kits for determining the dose threshold to a polyvalent agent needed in a patient in need of treatment. The dose of polyvalent agent that induces cell membrane wounding in a mammal can be determined by providing a kit comprising a sufficient amount of the polyvalent agent that binds to a highly expressed cell surface antigen to perform binding assays or to determine the amount of cell wounding and/or killing induced by the polyvalent agent. In an additional embodiment, a kit is provided for determining the dose threshold to a cell membrane wounding antibody in a mammal, comprising a sufficient amount of a cell wounding antibody that binds to a highly expressed cell surface antigen to perform binding assays or to determine the amount of cell wounding and/or killing induced by the polyvalent agent. The kits can also comprise a crosslinking agent, or a cytotoxic agent, or combinations thereof, for determining the dose threshold to the polyvalent agent in the presence of cytotoxic agents and/or a cell membrane wounding augmenting crosslinking agent. Typically the patient's own cells (e.g., blood cells, tumor cells, etc.) are obtained and tested using the reagents contained within the kits to determine the number of cell surface antigens expressed on the cells, as well as to determine the amount of wounding and/or cell killing provided by a predetermined amount of polyvalent agent.

X. Hyperproliferating Cells

Conditions characterized by hyperproliferation of cells include cancers, autoimmune diseases, viral infection and immunodeficiencies. Cancers can include cancers of any cell type or tissue. Preferred cancers include cancers of B cell origin, such as lymphomas and leukemias.

Autoimmune diseases include systemic lupus erythematosis, rheumatoid arthritis, autoimmune lymphoproliferative disease, multiple sclerosis, psoriasis, and myasthenia gravis, but can also include Hashimoto's thyroiditis, lupus nephritis, dermatomyositis, Sjogren's syndrome, Alzheimer's Disease, Sydenham's chorea, lupus nephritis, rheumatic fever, polyglandular syndromes, bullous pemphigoid, diabetes mellitus, Henoch-Schonlein purpura, post-streptococcal nephritis, erythema nodosum, Takayasu's arteritis, Addison's disease, Crohn's disease, sarcoidosis, ulcerative colitis, erythema multiforme, IgA nephropathy, polyarteritis nodosa, ankylosing spondylitis, Goodpasture's syndrome, thromboangitis ubiterans, primary biliary cirrhosis, thyrotoxicosis, scleroderma, chronic active hepatitis, polymyositis/dermatomyositis, polychondritis, pamphigus vulgaris, Wegener's granulomatosis, membranous nephropathy, amyotrophic lateral sclerosis, tabes dorsalis, giant cell arteritis/polymyalgia, pernicious anemia, rapidly progressive glomerulonephritis, fibrosing alveolitis, Class III autoimmune diseases such as immune-mediated thrombocytopenias, such as acute idiopathic thrombocytopenic purpura and chronic idiopathic thrombocytopenic purpura, and the like.

Viral infection can also cause cellular hyperproliferative conditions and disorders in numerous cell types and tissues. Examples of virus infections that induce hyperproliferation include human immunodeficiency virus (HIV) infection, including HTLV-1, HTLV-2, Epstein Barr virus (EBV) infection, human papilloma virus (HPV) infection, and the like.

XI. Combinations with Additional Cytotoxic Agents

The present inventors have made the surprising discovery that the toxicity of cell wounding antibodies can be markedly and even synergistically enhanced by the addition of a cytotoxic agent, including chemotherapeutic agents, radioactive isotopes, cytotoxic antibodies, immunoconjugates, ligand conjugates, immunosuppressants, cell growth regulators and/or inhibitors, toxins, or mixtures thereof.

The chemotherapeutic agents that can be used in the formulations and methods of the invention include taxanes, colchicine, vinca alkaloids, epipodophyllotoxins, camptothecins, antibiotics, platinum coordination complexes, alkylating agents, folic acid analogs, pyrimidine analogs, purine analogs or topoisomerase inhibitors. A preferred topoisomerase inhibitor is an epipodophyllotoxin. Preferred pyrimidine analogs include capecitabine, 5-fluoruracil, 5-fluorodeoxyuridine, 5-fluorodeoxyuridine monophosphate, cytosine arabinoside, 5-azacytidine, or 2',2'-difluorodeoxycytidine. Preferred purine analogs include mercaptopurine, azathioprene, thioguanine, pentostatin, erythrohydroxynonyladenine, cladribine, vidarabine, and fludarabine phosphate. Folic acid analogs include methotrexate, raltitrexed, lometrexol, permefrexed, edatrexate, and pemetrexed. A preferred epipodophyllotoxin is etoposide or teniposide. A preferred camptothecin is irinotocan, topotecan, or camptothecan. Preferably, the antibiotic is dactinomycin, daunorubicin (daunomycin, daunoxome), doxorubicin, idarubicin, epirubicin, valrubucin, mitoxanthrone, bleomycin, or mitomycin. A preferred platinum coordination complex is cisplatin, carboplatin, or oxaliplatin. Preferably, the alkylating agent is mechlorethamine, cyclophosphamide, ifosfamide, melphalan, dacarbazine, temozolomide, thiotepa, hexamethylmelamine, streptozocin, carmustine, busulfan, altretamine or chlorambucil.

Additional examples of chemotherapeutic agents include alkylating agents such as thiotepa and cyclosphosphamide (CYTOXAN™);

alkyl sulfonates such as busulfan, improsulfan and piposulfan;

aziridines such as benzodopa, carboquone, meturedopa, and uredopa;

ethylenimines and methylamelamines including altretamine, triethylenemelamine, trietylenephosphoramide, triethylenethiophosphoramide and trimethylolomelamine;

acetogenins (especially bullatacin and bullatacinone);

camptothecins (including the synthetic analogue topotecan);

bryostatin; callystatin; CC-1065 (including its adozelesin, carzelesin and bizelesin synthetic analogues);

cryptophycins (particularly cryptophycin 1 and cryptophycin 8);

dolastatin; duocarmycin (including the synthetic analogues, KW-2189 and CBI-TMI);

eleutherobin; pancratistatin; sarcodictyin; spongistatin;

nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard;

nitrosureas such as carmustine, chlorozotocin, fotemustine, lomustine, nimustine, ranimustine;

antibiotics such as the enediyne antibiotics (e.g. calicheamicin, especially calicheamicin gamma1I and calicheamicin phiI1, see, e.g., Agnew (1994) Chem. Intl. Ed. Engl., 33, 183-186; dynemicin, including dynemicin A; bisphosphonates, such as clodronate; esperamicin; as well as neocarzinostatin chromophore and related chromoprotein enediyne antibiotic chromomophores), aclacinomysins, actinomycin, authramycin, azaserine, bleomycins, cactinomycin, carabicin, carminomycin, carzinophilin, chromomycins, dactinomycin, daunorubicin, detorubicin, 6-diazo-5-oxo-L-norleucine, doxorubicin (Adriamycin™) (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin;

anti-metabolites such as methotrexate and 5-fluorouracil (5-FU);

folic acid analogues such as denopterin, methotrexate, pteropterin, trimetrexate;

folic acid replenisher such as folinic acid;

purine analogs such as fludarabine, 6-mercaptopurine, thiamiprine, thioguanine;

pyrimidine analogs such as ancitabine, azacitidine, 6-azauridine, carmofur, cytarabine, dideoxyuridine, doxifluridine, enocitabine, floxuridine;

androgens such as calusterone, dromostanolone propionate, epitiostanol, mepitiostane, testolactone;

anti-adrenals such as aminoglutethimide, mitotane, trilostane;

aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidamine; maytansinoids such as maytansine and ansamitocins; mitoguazone; mitoxantrone; mopidamol; nitracrine; pentostatin; phenamet; pirarubicin; losoxantrone; podophyllinic acid; 2-ethylhydrazide; procarbazine; PSK®; razoxane; rhizoxin; sizofiran; spirogermanium; tenuazonic acid; triaziquone; 2,2',2'-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; cytosine, arabinoside ("Ara-C");

cyclophosphamide; thiotepa; taxoids, e.g. paclitaxel (TAXOL®, Bristol-Myers Squibb Oncology, Princeton, N.J.) and doxetaxel (TAXOTERE®, Rhone-Poulenc Rorer, Antony, France); chlorambucil; gemcitabine (Gemzar™); 6-thioguanine; mercaptopurine; methotrexate;

platinum analogs such as cisplatin and carboplatin;

vinblastine, vincristine; vinorelbine (Navelbine™);

etoposide (VP-16); ifosfamide; mitoxantrone; novantrone; teniposide; edatrexate; daunomycin; aminopterin; xeloda; ibandronate; CPT-11;

topoisomerase inhibitor RFS 2000; difluoromethylornithine (DMFO);

retinoids such as retinoic acid; capecitabine; and pharmaceutically acceptable salts, acids or derivatives of any of the above.

Particularly preferred are agents that interfere with the polymerization or depolymerization of microtubules. Exemplary agents include colchicine, the vinca alkaloids, such as vincristine, vinblastine, vindesine, or vinorelbine, and taxanes, such as taxol, paclitaxel, and docetaxel. Mixtures of any of the above agents can also be used.

Additional preferred agents are anti-actin agents. In a preferred embodiment, the anti-actin agent is jasplakinolide or cytochalasin, and is used in an ex vivo treatment, for example, to purge bone marrow of neoplastic cells.

Toxins can be administered as immunoconjugates, ligand conjugates, or co-administered with an antibody. Toxins include, without limitation, *Pseudomonas* exotoxin A, ricin, diphtheria toxin, momordin, pokeweed antiviral protein, *Staphylococcal* enterotoxin A, gelonin, maytansinoids (e.g., as described in U.S. Pat. No. 6,441,163), or the like.

XII. Antibodies

Cell wounding antibodies useful in the present invention can include antibodies to any highly expressed cell surface antigen. Cell surface antigens include cell surface expressed molecules such as receptors, immunoglobulins, cytokines, glycoproteins, etc. Preferred cell surface antigens are associated with the cytoskeleton.

Preferred cell wounding antibodies include antibodies to cell surface antigens that are associated with the cytoskeleton, as this feature appears to enhance the cell wounding. Preferred cell wounding antibodies include VH4-34 gene encoded antibodies, for example, anti-CDIM antibodies. As discussed previously, the term "antibodies" is used in its broadest sense and includes antibody fragments that do not bear an Fc portion (e.g., non-Fc bearing antibodies). Examples of antibodies and antibody fragments can include Fab, Fab', F(ab')$_2$, and Fv fragments; diabodies; linear antibodies (Zapata, et al. (1995) *Protein Eng.* 8(10), 1057-1062) single-chain antibody molecules; and multispecific antibodies formed from antibody fragments. The term "antibodies" and "antibody fragments" includes hereafter developed agents that exhibit antibody binding characteristics such as these described. Preferably, the antibodies and antibody fragments can be further crosslinked with a crosslinking agent, such as an antibody having specific binding for a portion of the cell wounding antibodies or cell wounding antibody fragments, so long as the crosslinking antibody binding does not interfere with the binding of the cell wounding antibodies or antibody fragments to the cell surface antigen. In a preferred embodiment, the crosslinking agent is a crosslinking antibody that binds to the cell wounding antibody bound to the cell. Preferably, the crosslinking antibody does not interfere with the binding of the cell wounding antibody. In one embodiment, the cell wounding antibody comprises an Fc portion, and the crosslinking agent binds to the Fc portion of the cell wounding antibody. In an additional embodiment, the crosslinking agent binds to a portion of the antibody other than the Fc portion, if present.

In a preferred embodiment, the cell wounding antibody is a VH4-34 antibody, preferably an anti-CDIM antibody. The anti-CDIM antibody can be used to wound, permeabilize or kill cells. In a particular embodiment, the anti-CDIM antibody is an antibody fragment, e.g., Fab$_2$' and can be crosslinked by an antibody having specific binding for the anti-CDIM antibody (e.g., 9G4). Preferably, the crosslinking antibody does not prevent binding of the anti-CDIM antibody to the CDIM epitope on the cell and provides crosslinking of the anti-CDIM antibody bound to the CDIM epitope on the cell.

The anti-CDIM antibodies can be used in conjunction with additional cytotoxic antibodies having specific binding for cell surface molecules on cells, e.g., B cells. The anti-CDIM antibodies and additional cytotoxic antibodies can be used in a combination treatment regimen. In a preferred embodiment, the cytotoxic antibody can have specific binding for any cell surface molecule on a B cell. For example, the cytotoxic antibody can exhibit specific binding for cell surface molecules on B cells, such as CD11a, CD19, CD20, CD21, CD22, CD25, CD34, CD37, CD38, CD40, CD45, CD52, CD80, CD 86, IL-4R, IL-6R, IL-8R, IL-13, IL-13R, α-4/β-1 integrin (VLA4), BLYS receptor, cell surface idiotypic Ig, tumor necrosis factor (TNF), or mixtures thereof, without limitation. For example, the cytotoxic antibody having specific binding for CD11a can be, for example, efalizumab (RAPTIVA). The cytotoxic antibody having specific binding for CD20 can be rituximab (RITUXAN). The cytotoxic antibody having specific binding for CD22 can be, for example, epratuzumab. The cytotoxic antibody having specific binding for CD25 can be, for example, daclizumab (ZENAPAX) or basiliximab (SIMULECT). Antibodies to CD52 include, e.g., CAMPATH. Antibodies to α-4/β-1 integrin (VLA4) include, e.g., natalizumab. Antibodies to TNF include, for example, infliximab (REMICADE).

Thus in preferred embodiments, the antibody having specific binding for CDIM epitopes on a B cell can be used in a combined immunotherapy regimen with RITUXAN, ZENAPAX, REMICADE or RAPTIVA, for example, or in combinations thereof. The cytotoxic antibody can also be used as an immunoconjugate comprising a radioactive isotope or toxin, for example. Further, in additional embodiments, a combined therapy can be used comprising the antibody having specific binding for CDIM epitopes on a B cell, an additional cytotoxic antibody having specific binding for cell surface molecules on a B cell, and one or more chemotherapeutic agents. For example, mAb216 could be used in combination with an anti-CD20 antibody such as rituximab, tosutimab, or ibritumomab, with an anti-CD22 antibody, such as, epratuzumab, or in combination with an anti-CD52 antibody such as CAMPATH. The combination therapy can further include chemotherapy, such as an agent that disrupts the cytoskeleton of the cell, e.g., vincristine, in a combined chemotherapy and immunotherapy regimen.

XIII. Radioactive Isotopes

The isotopes used to produce therapeutically useful immuno- or ligand conjugates typically produce high energy α-, β- or β-particles which have a therapeutically effective path length. Such radionuclides kill cells to which they are in close proximity, for example neoplastic cells to which the conjugate is bound. The advantage of targeted delivery is that the radioactively labeled antibody or ligand generally has little or no effect on cells not in the immediate proximity of the targeted cell.

With respect to the use of radioactive isotopes as cytotoxic agents, modified antibodies or ligands may be directly labeled (such as through iodination) or may be labeled using of a chelating agent. In either method, the antibody or ligand is labeled with at least one radionuclide. Particularly preferred chelating agents comprise 1-isothiocyamatobenzyl-3-methyldiothelene triaminepentaacetic acid ("MX-DTPA") and cyclohexyl diethylenetriamine pentaacetic acid ("CHX-DTPA") derivatives. Other chelating agents comprise P-DOTA and EDTA derivatives. Particularly preferred radionuclides for indirect labeling include $^{111}$In and $^{90}$Y.

The radioactive isotope can be attached to specific sites on the antibody or ligand, such as the N-linked sugar resides present only on the Fc portion of the antibody. Technetium-99m labeled antibodies or ligands may be prepared by ligand exchange processes or by batch labeling processes. For example, the antibody can be labeled by reducing pertechnate (TcO$_4$) with stannous ion solution, chelating the reduced technetium onto a Sephadex column and applying the antibody to this column. Batch labeling techniques include, for example, incubating pertechnate, a reducing agent such as $SnCl_2$, a buffer solution such as a sodium-potassium phthalate-solution, and the antibody. Preferred radionuclides for labeling are well known in the art. An exemplary radionuclide for labeling is $^{131}I$ covalently attached via tyrosine residues. Radioactively labeled antibodies according to the invention can be prepared with radioactive sodium or potassium iodide and a chemical oxidizing agent, such as sodium hypochlorite, chloramine T or the like, or an enzymatic oxidizing agent, such as lactoperoxidase, glucose oxidase and glucose.

Patents relating to chelators and chelator conjugates are known in the art. For example, U.S. Pat. No. 4,831,175 to Gansow is directed to polysubstituted diethylenetriaminepentaacetic acid chelate and protein conjugates containing the same and methods for their preparation. U.S. Pat. Nos. 5,099,069, 5,246,692, 5,286,850, 5,434,287 and 5,124,471 all to Gansow also relate to polysubstituted DTPA chelates. These patents are incorporated herein by reference in their entireties. Other examples of compatible metal chelators are ethylenediaminetetraacetic acid (EDTA), diethylenetriaminepentaacetic acid (DPTA), 1,4,8,11-tetraazatetradecane, 1,4,8,11 tetraazatetradecane-1,4,8,11-tetraacetic acid, 1-oxa-4,7,12,15-tetraazaheptadecane, 4,7,12,15-tetraacetic acid, or the like. Cyclohexyl-DTPA or CHX-DTPA is particularly preferred. Still other compatible chelators, including those yet to be discovered, may easily be discerned by a skilled artisan and are clearly within the scope of the present invention. Additional chelators include the specific bifunctional chelators described in U.S. Pat. Nos. 6,682,734, 6,399,061 and 5,843,439, and are preferably selected to provide high affinity for trivalent metals, exhibit increased tumor-to-non-tumor ratios and decreased bone uptake as well as greater in vivo retention of radionuclide at target sites, i.e., B-cell lymphoma tumor sites. However, other bifunctional chelators that may or may not possess all of these characteristics are known in the art and may also be beneficial in tumor therapy.

Modified antibodies can also be conjugated to radioactive labels for diagnostic as well as therapeutic purposes. Radiolabeled therapeutic conjugates for diagnostic "imaging" of tumors can also be utilized before administration of antibody and cytotoxic agent to a patient. For example, the monoclonal antibody binding the human CD20 antigen known as C2B8 can be radiolabeled with $^{111}In$ using a bifunctional chelator, such as MX-DTPA (diethylenetriaminepentaacetic acid), which comprises a 1:1 mixture of 1-isothiocyanatobenzyl-3-methyl-DTPA and 1-methyl-3-isothiocyanatobenzyl-DTPA. $^{111}In$ is a preferred diagnostic radioactive isotope since between about 1 and about 10 mCi can be safely administered without detectable toxicity, and the imaging data is an indicator of subsequent $^{90}Y$-labeled antibody distribution. A typical dose of $^{111}In$-labeled antibody of 5 mCi for imaging studies is used, and optimal imaging can be determined at various times after administration of the labeled antibody or ligand, typically three to six days after administration. See, for example, Murray, J. (1985) *Nuc. Med.* 26, 3328 and Carraguillo et al., (1985) *J. Nuc. Med.* 26, 67.

A variety of radioactive isotopes can be utilized and one skilled in the art can readily determine which radioactive isotope is most appropriate under various conditions. For example, $^{131}I$ is frequently utilized for targeted immunotherapy. However, the clinical usefulness of $^{131}I$ can be limited by its short half life (8 days), the potential for dehalogenation of iodinated antibody both in the blood and at tumor or sites, and its high energy γ emission which may not provide sufficiently localized dose deposition in tumor, depending on tumor size, as desired. With the advent of additional chelating agents, additional opportunities are provided for attaching metal chelating groups to proteins and utilizing other radionuclides such as $^{111}In$ and $^{90}Y$. $^{90}Y$ provides several benefits for utilization in radioimmunotherapeutic applications. For example, the longer useful half life of 64 hours for $^{90}Y$ is sufficiently long to allow antibody accumulation by tumor cells and, unlike $^{131}I$, $^{90}Y$ is a pure beta emitter of high energy with no accompanying gamma radiation in its decay, having a range in tissue of 100 to 1,000 cell diameters. Furthermore, the minimal amount of penetrating radiation allows for outpatient administration of $^{90}Y$-labeled antibodies. Additionally, internalization of labeled antibody is not required for cell killing, and the ionizing radiation should be lethal for adjacent tumor cells lacking the target antigen.

Effective single treatment dosages (i.e., therapeutically effective amounts) of $^{90}Y$-labeled antibodies range from between about 5 and about 75 mCi, more preferably between about 10 and about 40 mCi. Effective single treatment non-marrow ablative dosages of $^{131}I$-labeled antibodies range from between about 5 and about 70 mCi, more preferably between about 5 and about 40 mCi. Effective single treatment ablative dosages (i.e., that may require autologous bone marrow transplantation) of $^{131}I$ labeled antibodies range from between about 30 and about 600 mCi, more preferably between about 50 and less than about 500 mCi. When the antibody or ligand has a longer circulating half life relative to a foreign protein such as a murine antibody, an effective single treatment non-marrow ablative dosage of $^{131}I$ labeled antibody ranges from between about 5 and about 40 mCi, more preferably less than about 30 mCi. Imaging dosages for a radioactive isotope label, e.g., the $^{111}In$ label, are typically less than about 5 mCi.

While $^{131}I$ and $^{90}Y$ have been used extensively in the clinic, other radioactive isotopes are known in the art and can been used for similar purposes. Still other radioisotopes are used for imaging. For example, additional radioisotopes which can be used include, but are not limited to, $^{131}I$, $^{125}I$, $^{123}I$, $^{90}Y$, $^{111}In$, $^{105}Rh$, $^{153}Sm$, $^{166}Ho$, $^{177}Lu$, and $^{188}Re$ and $^{186}R$, $^{32}P$, $^{57}Co$, $^{64}Cu$, $^{67}Cu$, $^{77}Ga$, $^{81}Rb$, $^{81}Kr$, $^{87}Sr$, $^{113}In$, $^{127}Cs$, $^{132}I$, $^{197}Hg$, $^{213}Pb$, $^{216}Bi$, $^{117}Lu$, $^{212}Pb$, $^{212}Bi$, $^{47}Sc$, $^{105}Rh$, $^{109}Pd$, $^{199}Au$, $^{225}Ac$, $^{211}At$, and $^{213}Bi$, In this respect alpha, gamma and beta emitters are all contemplated as aspects of the instant invention. Further, it is submitted that one skilled in the art could readily determine which radionuclides are compatible with a selected course of treatment without undue experimentation. To this end, additional radionuclides which have already been used in clinical diagnosis include $^{125}I$, $^{123}I$, $^{99}Tc$, $^{43}K$, $^{52}Fe$, $^{67}Ga$, $^{68}Ga$, as well as $^{111}In$. Antibodies have also been labeled with a variety of radionuclides for potential use in targeted immunotherapy, for example, as described in Peitersz et al. (1987) *Immunol. Cell Biol.* 65, 111-125. These radioactive isotopes include $^{188}Re$ and $^{186}Re$ as well as $^{199}Au$ and $^{67}Cu$. U.S. Pat. No. 5,460,785 provides information regarding such radioisotopes and is incorporated herein by reference.

XIV. Cell Growth Regulators and/or Inhibitors

Cell growth regulators and/or inhibitors include small molecule therapeutics such as hormones or anti-hormonal agents, kinase inhibitors, proteasome inhibitors, gene therapy agents or gene expression modifiers.

Anti-hormonal agents can be useful particularly in the therapy of autoimmune diseases where hormonal exacerbation is implicated, particularly estrogenic action in women. Anti-hormonal agents act to regulate or inhibit hormone action on tumors such as anti-estrogens and selective estrogen receptor modulators (SERMs), including, for example, tamoxifen (including Nolvadex™), raloxifene, droloxifene, 4-hydroxytamoxifen, trioxifene, keoxifene, LY117018, onapristone, and toremifene (Fareston™); aromatase inhibitors that inhibit the enzyme aromatase, which regulates estrogen production in the adrenal glands, such as, for example, 4(5)-imidazoles, aminoglutethimide, megestrol acetate (Megace™), exemestane, formestane, fadrozole, vorozole (Rivisor™), letrozole (Femara™), and anastrozole (Arimidex™); and anti-androgens such as flutamide, nilutamide, bicalutamide, leuprolide, and goserelin; and pharmaceutically acceptable salts, acids or derivatives of any of the above. Androgenic hormones can be especially useful in the treatment of autoimmune disease, and a representative androgenic hormone is dihydroepiandrosterone (DHEA). Selective androgen receptor modulators (SARMs) include for example, the compounds described in U.S. Pat. No. 6,645,974 to Hutchinson, such as androstane and androstene carboxamides.

Kinase inhibitors are widely known, and particularly preferred kinase inhibitors include the bcr/abl tyrosine kinase inhibitors, such as imatinib (Gleevec) and its related compounds, as described in U.S. Pat. No. 5,521,184 to Zimmermann. Additional tyrosine kinase inhibitors can include agents that block signaling complexes involved in the activation of and transcription of Lyn kinase, including for example, siRNAs that blocks the activity of Lyn kinase. Yet additional kinase inhibitors include compounds such as AGL 2592 described in Ben-Bassat, H. et al. (2002) *J. Pharmacol. Exp. Ther.* 303, 163 shown to be apoptosis inducing for non-Hodgkin lymphomas; herbimycin A as described by Mahon, T M and O'Neill, L A (1995) *J. Biol. Chem.* 270, 28557 shown to block DNA binding and NF-kappa B-driven gene expression; indolinone compounds such as those described in U.S. Pat. No. 6,680,335 to Tang; pyrazolopyrimidine derivatives such as those described in U.S. Pat. No. 6,660,744 to Hirst, and the like. Proteasome inhibitors include the boronic esters described in U.S. Pat. No. 6,083,903 to Adams. A preferred proteasome inhibitor is bortezomib (Velcade).

Gene therapy agents and gene expression modifiers include antisense nucleic acid sequences, interfering nucleic acid sequences and the like. The gene therapy agents and gene expression modifiers can be used either as an immunoconjugate or as a separately administered cytotoxic agent. Particularly useful gene therapy agents and gene expression modifiers include those that encode proteins involved in pro-apoptotic pathways, as well as those that block inhibitors of the pro-apoptotic pathways or those that block proliferative signaling, all of which can contribute to uncontrolled growth and hyperproliferation. For example, gene expression modifiers can include antisense or siRNA that act to inhibit the NF-kB pathway, thereby inhibiting the abnormal proliferation present when this pathway is abnormally activated.

Antisense DNA oligonucleotides are typically composed of sequences complementary to the target sequence, usually a messenger RNA (mRNA) or an mRNA precursor. The mRNA contains genetic information in the functional, or sense, orientation and binding of the antisense oligonucleotide inactivates the intended mRNA and prevents its translation into protein. Such antisense molecules are determined based on biochemical experiments showing that proteins are translated from specific RNAs and once the sequence of the RNA is known, an antisense molecule that will bind to it through complementary Watson-Crick base pairs can be designed. Such antisense molecules typically contain between 10-30 base pairs, more preferably between 10-25, and most preferably between 15-20. The antisense oligonucleotide can be modified for improved resistance to nuclease hydrolysis, and such analogues include phosphorothioate, methylphosphonate, phosphoroselenoate, phosphodiester and p-ethoxy oligonucleotides as described in WO 97/07784.

The gene therapy agent can also be a ribozyme, DNAzyme, catalytic RNA, or a small interfering RNA (siRNA). RNA interference utilizes short RNAs typically less than about 30 base pairs, which act through complementary base pairing as described above. The siRNAs can be linear or circular.

As mentioned above, agents and modifiers that block signaling complexes involved in the activation of and transcription of Lyn kinase, would be advantageous. In a particular embodiment, an siRNA that blocks the activity of Lyn kinase, such as the siRNA reported by Ptasznik, A et al., (2004) *Nat. Med.* 10, 1187, can be administered with the anti-CDIM binding antibody either as an immunoconjugate or as a separately administered cytotoxic agent.

XV. Pharmaceutical Formulations

Antibodies, and cytotoxic agents can be formulated using any methods and pharmaceutically acceptable excipients known in the art. Typically, antibodies are provided in saline, with optional excipients and stabilizers. Chemotherapeutic agents can vary widely in formulation methods and excipients, and this information is available for example, in *Remington's Pharmaceutical Sciences* (Arthur Osol, Editor).

It is contemplated that the methods and compositions described herein can be used in in vivo, ex vivo and in vitro applications.

The compositions of the invention may be administered to the patient by a variety of different means. The means of administration will vary depending upon the intended application. As one skilled in the art would recognize, administration of the compositions can be carried out in various fashions, for example, via topical administration, including, but not limited to, dermal, ocular and rectal; transdermal, via passive or active means, e.g., using a patch, a carrier, or iontophoresis; transmucosal, e.g., sublingual, buccal, rectal, vaginal, or transurethral; oral, e.g., gastric or duodenal; parenteral injection into body cavity or vessel, e.g., intraperitoneal, intravenous, intralymphatic, intratumoral, intramuscular, interstitial, intraarterial, subcutaneous, intralesional, intraocular, intrasynovial, intraarticular; via inhalation, e.g., pulmonary or nasal inhalation, using e.g., a nebulizer. Compositions and methods wherein the polyvalent agent is an antibody are generally administered parenterally.

It is to be understood that while the invention has been described in conjunction with the preferred specific embodiments thereof, that the description above as well as the examples that follow are intended to illustrate and not limit the scope of the invention. The practice of the present invention will employ, unless otherwise indicated, conventional techniques of organic chemistry, polymer chemistry, biochemistry and the like, which are within the skill of the art. Other aspects, advantages and modifications within the scope of the invention will be apparent to those skilled in the art to which the invention pertains. Such techniques are explained fully in the literature.

All patents, patent applications, and publications mentioned herein, both supra and infra, are hereby incorporated by reference.

In the following examples, efforts have been made to ensure accuracy with respect to numbers used (e.g., amounts, temperature, etc.) but some experimental error and deviation should be accounted for. Unless indicated otherwise, temperature is in degrees ° C. and pressure is at or near atmospheric.

| Abbreviations: | |
|---|---|
| ALL | acute lymphoblastic leukemia |
| ASPR | Asparaginase |
| BCR | B-cell receptor |
| BFA | Brefeldin A |
| DNR | Daunorubicin |
| FITC | Fluorescein isothiocyanate |
| IM | Infectious mononucleosis |
| mAb | Monoclonal antibody |
| PI | Propidium iodide |
| RBC | Red blood cells |
| SLE | Systemic lupus erythematosus |
| VCR | Vincristine |
| WBC | White blood cell |

Example 1 mAb 216 Wounds B Cell Membranes and Invokes a Resealing Response by Lysosomes

The natural response to membrane damage is rapid resealing by addition of internal lysosomal membrane at the wound site. Lamp-1 is an abundant lysosomal membrane glycoprotein normally not present on the plasma membrane (Granger, B. L., et al. (1990) *J. Biol. Chem.* 265, 12036; McNeil, P. L. (2002) *J. Cell Sci.* 115, 873). When lysosomes are induced to fuse with plasma membrane, the intra-lysosomal $NH_2$-terminal domain of Lamp-1 becomes exposed on the cell surface. This fusion event can be monitored by surface staining of live cells with mAbs directed to the lumenal epitope of Lamp-1 (Reddy, A., et al. (2001) *Cell* 106, 157; Rodriguez, A., et al. (1997) *J. Cell. Biol.* 137, 93; Martinez, I., et al. (2000) *J. Cell. Biol.* 148, 1141). Thus, the presence of Lamp-1 on the cell surface is an indication of membrane resealing following membrane disruption (McNeil, P. L., and R. A. Steinhardt (2003) *Ann. Rev. Cell Dev. Biol.* 19, 697).

To test whether the VH4-34 encoded mAb 216 wounds cells and thus invokes a rapid repair and resealing response, human B cell lines treated with mAb 216 were assayed for the swift appearance on the cell surface of the lysosome-specific protein Lamp-1.

Cells and Reagents

Human Pre-B cell line Nalm-6 (Hurwitz, R., et al. (1979) *Int. J. Cancer* 23, 174), Reh (Rosenfield, C., A. et al. (1977) *Nature* 267, 841), and mature B-cell line OCI-Ly8 Tweeddale, M. E., et al. (1987) *Blood* 69, 1307) were maintained in logarithmic phase in Iscove's medium with heat inactivated 10% FCS. B cell lines were obtained from ATCC. VH4-34 encoded mAbs, mAb 216 (Bhat, N. M., et al. (1993) *J. Immunol.* 151, 5011), Z2D2 (Bhat, N. M., et al. (2000) *Scand. J. Immunol.* 51, 134), and Y2K as well as isotype-matched control mAb, MS2B6, derived from a member of the VH3 family (Glasky, M. S., et al. (1992) *Hum. Antibod. Hybridomas* 3, 114), were produced in the laboratory and purified from serum free hybridoma supernatant by 2× precipitation with water. MAbs were concentrated when necessary on a Centriprep concentrator (Amnicon, Dancers, Mass.). Purity of the IgM mAbs, checked by polyacrylamide gel electrophoresis, was 90-95% pure. Concentration of purified IgMs was determined by sandwich ELISA using human IgM as a standard (catalog #31146, Pierce Biochemicals, Rockford, Ill.). In addition to MS2B6, the Pierce IgM was also used as an isotype control. All mAbs were sterile-filtered and free of sodium azide.

Cell Viability Assay Using PI Staining and Forward Scatter

The integrity of the plasma membrane was assessed by the ability of cells to exclude propidium iodide (PI, Sigma, St. Louis, Mo.). The level of PI incorporation was quantitated by flow cytometry on FACScan (Becton-Dickinson, San Jose Calif.) interfaced with VersatermPro and FlowJo software at Stanford's FACS facility. PI-negative cells with normal size as measured by forward scatter signals were considered live cells.

Briefly, cells were treated as specified in each experiment and resuspended in PBS with 3% FCS and 10 µgs/ml of PI. In experiments where toxicity was evaluated in Ca-free medium, cells were resuspended in appropriate media with or without calcium to which 10 µgs/ml PI was added. Since previous studies have shown that mAb 216-mediated toxicity is remarkably pronounced at lower temperatures (Bhat, N. M., et al. (1996) *Clin. Exp. Immunol* 105, 183), precautions were taken to keep all media and cells at 37° C. and the centrifuge at room temperature.

ATP Depletion and Release Assay

Intracellular and released ATP was measured according to manufacturer's instructions by the bioluminescence assay kit (Catalog # A-22066, Molecular Probes). Standard ATP dilutions ranging from 1 nM to 1 µM were tested as positive control. Cells were exposed to various concentrations of mAb 216, in different media as specified in each experiment. 10 µl of reaction supernatant was added to 90 µl of the standard reaction solution that contained DTT, luciferin and luciferase. Light generation, in the presence of ATP as a cosubstrate, was immediately measured by luminometer (Lumimark Microplate Reader, Bio-Rad) interfaced with MicroWin 2000, version 4.2 software (Mikrotek Laborsysteme, Gmbh). This assay allows detection of femtomolar quantities of ATP. To assess the intracellular ATP content, cells were lysed with 1% NP-40 at RT for 10 minutes, and 10 µl of the lysate was tested as described above.

Lamp-1 Expression Studies

Surface Lamp-1 expression was studied by epi-fluorescence, flow cytometry and confocal microscopy. Antibodies to the lumenal epitope of human Lamp-1 (CD107a, clone H4A3) and the isotype control for Lamp-1, a mouse $IgG_1k$ were obtained from BD-PharMingen. Both antibodies were detected with a secondary FITC-conjugated Goat $F(ab)_2$ anti-mouse IgG (Pierce Biochemicals). Cells ($5\times10^5$) were exposed to various concentrations of mAb 216 or human IgM control (mAb MS2B6 or Pierce IgM) for the specified time in each experiment at 37° C. Cells were then fixed with 2% pre-warmed paraformaldehyde at RT for 20 minutes, washed twice with pre-warmed media and stained with anti-Lamp-1 or isotype control for 15 minutes. Cells were then washed twice with staining medium (PBS with 3% FCS and 0.2% sodium azide) and incubated with secondary antibody to anti-Lamp-1 for another 15 minutes. After two washings, cells were resuspended in staining medium and analyzed by flow cytometry, immunofluorescence or confocal microscopy.

Confocal imaging was performed at Stanford's Cell Sciences Imaging Facility on the MultiProbe 2010 laser confocal microscope (Molecular Dynamics, Sunnyvale, Calif.). The MultiProbe uses an Ar/Kr mixed gas laser with excitation lines of 488, 568 and 647 and is built on a Nikon Diaphot 200 inverted microscope. With an excitation wavelength of 488 nm, the emitted light was passed through a 510LP beamsplitter and collected with a 510 long pass filter. A Nikon 60X (NA1.4) planapo objective was used. Epi-fluorescence imaging was performed on Axioplan 2 Microscope (Carl Zeiss, Inc., GmbH) equipped with AxioCam HRc camera (Carl Zeiss) and Opti-Quip Power Supply (Model 1200, Highland Mills, N.Y.) interfaced with Axiovision 3.1 software (Carl Zeiss). Flow cytometry was performed on FACScan.

Results and Conclusions

Lamp-1 expression on untreated cells varied from as low as 5% to 50% from experiment to experiment. The variation occurs due to standard laboratory handling of B cell lines. In experiments where baseline level of lamp-i expression was 50%, isotype control treated cells remained 50% positive and mAb 216 treated cells were 100% Lamp-1 positive. Lamp-1 staining on cell lines was repeated 5 times to ensure reproducibility. Results are discussed from experiments where baseline Lamp-1 expression is 5%.

Nalm-6 cells exposed to mAb 216 for 1 minute demonstrated a dramatic increase in Lamp-1 staining, but cells exposed to isotype control or cells with no treatment did not increase their lamp-1 expression. Lamp-1 exposure was also observed in other B cell lines, OCI-Ly8 (mature-B) and Reh by FACS and epi-fluorescence (data not shown). Membrane integrity of cells was simultaneously assessed for each sample by PI uptake. Cells remained PI negative at 1 minute post 216 exposure.

Figure 5A:
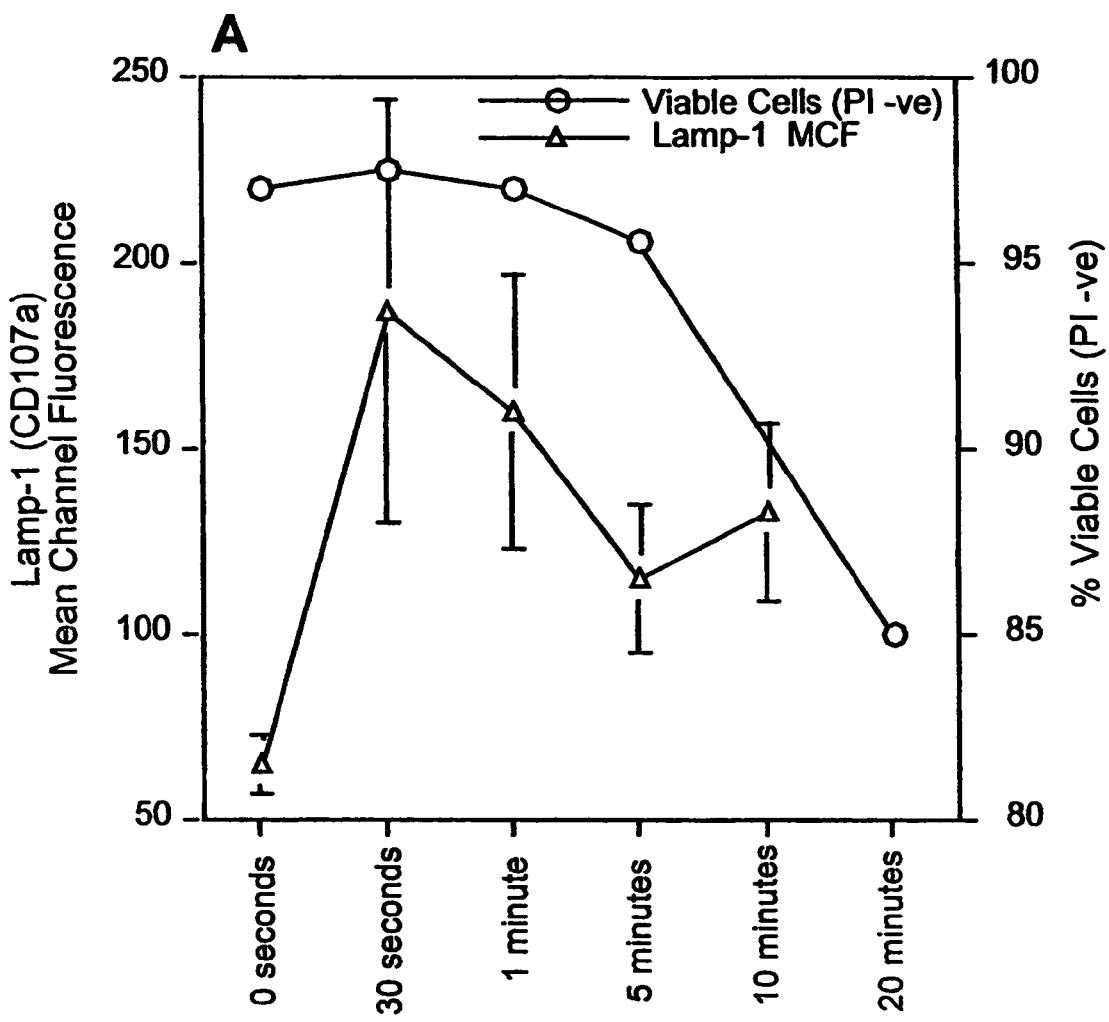
FIG. 5A illustrates the time course of the appearance of Lamp-1 on the surface of B cells treated with mAb 216 compared with the time course of the loss of cell viability.

Lamp-1 staining and PI uptake was also measured at different time points post mAb 216 exposure. Lamp-1 exposure was a rapid event with the brightest staining observed at 30 seconds of Ab exposure, dropping gradually in the next 5 minutes (FIG. 5A). Cells remained PI-negative during this time period. PI uptake was demonstrated after about 5 minutes of exposure to mAb 216, and by 20 minutes, 10-25% of cells became membrane permeable, as evinced by PI uptake.

Figure 5B:
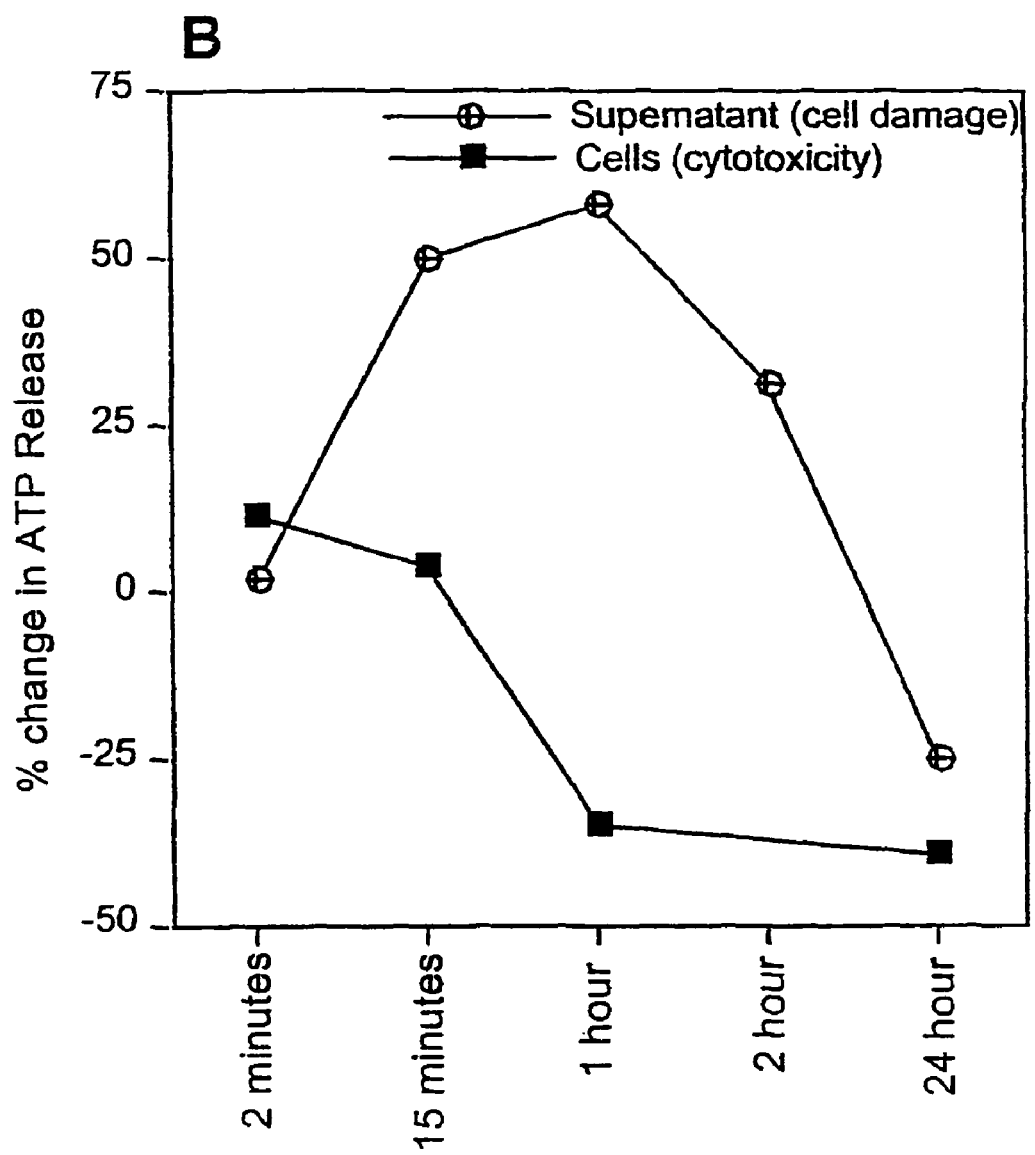
FIG. 5B illustrates the time course of release of ATP from damaged cells compared with the number of viable cells.

Membrane disruption measured by release of ATP also showed a similar time course. As shown in FIG. 5B, ATP was not detected in the supernatant at 2 minutes, a time-point where Lamp-1 is detected on the cell membrane. But at 15 minutes and 1 hr ATP release increased, suggesting membrane damage occurred that could not be resealed. At 2 and 24 hr post mAb 216-treatment, there was a decrease in measured ATP that may be the result of cell lysis and necrosis that degrades the released ATP. When ATP content in the cell pellet is evaluated, the bioluminescent assay becomes a measure of cell proliferation and cytotoxicity. The cytotoxic effects of mAb 216 were apparent within 1 hr of exposure.

These results demonstrate that mAb 216 mediated membrane damage is repaired by the same mechanism that restores cell viability after injury by mechanical or physical wounding, indicating that mAb 216 treatment results in a cell wounding event similar to any other large membrane disruption. Cell wounding by an antibody has not heretofore been observed. The membrane damage by mAb 216 was initially resealed as internal membrane was added rapidly to the lipid bilayer, but with increased time of exposure to mAb 216, attempts to reseal failed and the membrane became permeable to both PI and ATP. In addition to mAb 216, other anti-B-cell VH4-34 encoded IgM mAbs mediated similar membrane damage and invoked a similar resealing response by lysosomes.

Example 2

Repair of mAb 216 Induced Membrane Damage is Dependent on Functional Actin

As discussed by McNeil, P. ((2002) *J. Cell Sci.* 115, 873) and others, membrane wound repair involves actin dependent processes. To test whether repair of membrane wounding induced by mAb 216 utilizes actin dependent repair mechanisms, cells were treated with agents that affect actin polymerization, and the effect on the repair of the membrane wound induced by mAb 216 was assessed. Cells were treated with cytochalasin or jasplakinolide, two agents that have opposite effects on actin polymerization. Cytochalasin depolymerizes actin into monomers, whereas jasplakinolide, a cyclic peptide obtained from a marine sponge, immobilizes actin in its filamentous form. Both treatments hinder actin-based cytoskeletal activities.

Methods:

Cytochalasin was obtained from Sigma and jasplakinolide was obtained from Molecular Probes (Eugene, Oreg.). Caspase inhibitors, Ac-IETD-CHO and Ac-DEVD-CHO were obtained from PharMingen (San Diego, Calif.). Nalm-6 cells ($1\times10^6$ cells/ml) were treated with jasplakinolide (3 µgs/ml), cytochalasin (5 µgs/ml), or caspase inhibitors (10 µM) for 2 hr at 37° C. before treatment with mAb 216. Control samples with equivalent amounts of DMSO were set in parallel. Cells were then exposed to 25 µg of mAb 216 or control Ab and analyzed by flow cytometry.

Results:

Cells treated with cytochalasin or jasplakinolide and mAb 216 showed decreased viability (percent viable cells) and hence increased susceptibility to mAb 216, demonstrating a synergistic effect and indicating a requirement for functional actin in the repair process. Cells treated with cytochalasin or jasplakinolide and control antibodies did not show a decrease in viability. Data from one representative experiment is shown in FIG. 6B. Similar results were obtained from three other experiments.

Incubation of cells with the caspase inhibitors Ac-IETD-CHO and Ac-DEVD-CHO did not alter cell viability, indicating that the mechanism of cell death is not due to apoptosis.

These results further support the mechanism of antibody induced cell membrane wounding caused by exposure to these antibodies.

Example 3

Repair of mAb 216 Induced Membrane Damage is Dependent on Calcium

Since exocytosis of lysosomes is known to be a calcium dependent phenomenon (Miyake, K., and P. L. McNeil (1995) *J. Cell Biol.* 131, 1737; Bi, G. Q., et al. (1995) *J. Cell Biol.* 131, 1747), membrane wounding by mAb 216 and repair of the wound was tested in calcium free and normal calcium conditions. The cell viability of Nalm-6 cells when treated with two VH4-34 encoded mAbs, mAb 216 at 50, 25 and 12.5 ng/ml concentrations, and Y2K at 50 ng/ml, was tested in the presence of media with and without calcium. As shown in FIG. 6A, cell viability decreased significantly in the absence of calcium, indicating that calcium was necessary for the wound repair. Cells treated with control antibodies or no antibody did not show any change in cell viability in the presence or absence of calcium. Other B cell lines, OCI-Ly8 and Reh also showed a similar increase in cytotoxicity in calcium-free conditions (data not shown).

Example 4

Repair of mAb 216 Induced Membrane Damage is Dependent on Functional Golgi

Treatment with Brefeldin A (BFA) is known to result in release of golgi-associated coat proteins, redistribution of the golgi membrane into the endoplasmic reticulum and a block in secretion from golgi apparatus (Klausner, R. D., (1992) *J. Cell Biol.* 116, 1071). Newly formed lysosomes are not generated in BFA treated cells, thus providing a condition to test their requirement in wound repair. Therefore, the ability of newly formed lysosomes to aid in the repair of the membrane wounds induced by mAb 216 cells was tested by treating cells with BFA.

Methods:

Brefeldin-A was obtained from Sigma. Nalm-6 cells ($1\times10^6$ cells/ml) were treated with BFA (25 µg/ml) for 2 hr at 37° C. before treatment with mAb 216. Control samples with equivalent amounts of DMSO were set in parallel. Cells were then exposed to 25 µg of mAb 216 or control Ab and analyzed by flow cytometry.

Results:

As shown in FIG. 6B, the cell viability (percent viable cells) was decreased by the combination of BFA and mAb 216, demonstrating a synergistic effect on viability. BFA had no effect on the viability of cells treated with control antibodies. This result demonstrates that membrane repair was blocked by BFA, suggesting that newly generated lysosomes are necessary for membrane repair and the continued survival and integrity of mAb 216-wounded B-cell lines. This result thus further confirms that mAb 216 generates membrane wounds on B cells, and that the cells attempt to patch the wound utilizing lysosomal fusion with the plasma membrane. When the generation of additional lysosomes is inhibited by BFA, the repair process may not be adequate to maintain cell viability.

Example 5

Synergistic B Cell Killing with Vincristine

Enhanced cell killing was demonstrated when mAb 216 was combined with chemotherapeutic agents, particularly with vincristine, in cytotoxicity assays directed against B cell lines. Three cell lines which have been derived from ALL blasts of different genotype and phenotype, Nalm 6, REH, and SUPB15, were incubated with mAb 216 alone or in combination with vincristine (VCR), for 48 hours at 37° C.

As shown in FIG. 4, and Table 1 below, these results show that at low vincristine concentrations (0.2 ng/ml), no cell death occurred due to treatment with vincristine alone. However, when vincristine was combined with mAb 216, the percentage of B cells killed more than doubled; demonstrating a synergistic interaction. The cytotoxicity of mAb 216 for B-progenitor lymphoblasts, alone and in combination with chemotherapy, makes this antibody a promising reagent for further immunotherapy studies in childhood ALL.

Example 6

Enhanced Cytotoxicity of mAB 216 to B Cell Lines by Chemotherapeutic Agents

In vitro cytotoxicity of mAb216 in combination with single chemotherapeutic agents was tested. Three cell lines which have been derived from ALL blasts of different genotype and phenotype, Nalm 6, REH, and SUPB15, were incubated with mAb 216 alone or in combination with vincristine (VCR), daunorubicin (DNR), or L-asparaginase (ASPR). All of the chemotherapeutic agents when used in combination with mAb 216 resulted in a greater degree of cytotoxicity than was seen with either single agent chemotherapy or mAb 216 alone. However, the combination of vincristine with mAb 216 was most efficacious, resulting in a magnitude of cytotoxicity that was synergistic compared to the amount of cell killing induced by either vincristine or mAb 216 alone. The results are presented in Table 1 below. These results demonstrate enhanced cytotoxicity of mAb 216 in the presence of chemotherapeutic agents, in part at least because mAb 216 treatment results in permeabilization of the B cells and allows otherwise impermeable chemotherapeutic agents access to the cell interior.

TABLE 1

In vitro cytotoxicity of mAb216 in combination with chemotherapeutic agents

| Cell line/ Incubation time | Treatment | Live cells × $10^5$ | % change in live cells |
|---|---|---|---|
| Nalm 6 48 h | control | 13 | |
| | mAb 216 5 µg/ml | 10 | 23 |
| | VCR 0.2 ng/ml | 13 | 0 |
| | mAb 216 + VCR | 6 | 53 |
| Nalm 6 48 h | control | 8.2 | |
| | mAb 216 5 µg/ml | 5.6 | 31 |
| | DNR 5 ng/ml | 4.3 | 47 |
| | mAb 216 + DNR | 1.5 | 81 |
| Nalm 6 48 h | control | 11 | |
| | mAb 216 5 µg/ml | 7.1 | 35 |
| | VCR 2 ng/ml | 5 | 54 |
| | mAb 216 + VCR | 0.28 | 97 |
| Nalm 6 48 h | control | 12 | |
| | mAb 216 5 µg/ml | 5.1 | 57 |
| | ASPR 0.8 U/ml | 9.2 | 23 |
| | mAb 216 + ASPR | 3.2 | 73 |
| REH 48 h | control | 8.6 | |
| | mAb 216 5 µg/ml | 4.6 | 46 |
| | VCR 2 ng/ml | 4.2 | 86 |
| | mAb 216 + VCR | 0.45 | 94 |
| REH 48 h | control | 13 | |
| | mAb 216 5 µg/ml | 11 | 15 |
| | VCR 2 ng/ml | 7.7 | 40 |
| | mAb 216 + VCR | 0.9 | 93 |
| REH 48 h | control | 9.6 | |
| | mAb 216 5 µg/ml | 3.4 | 65 |
| | ASPR 0.8 U/ml | 6.2 | 35 |
| | mAb 216 + aspar. | 2.4 | 75 |
| SUP B15 48 h | control | 5.1 | |
| | mAb 216 5 µg/ml | 3.6 | 29 |
| | VCR 2 ng/ml | 2.8 | 45 |
| | DNR 4 ng/ml | 0.44 | 91 |
| | mAb 216 + VCR | 1.5 | 50 |
| | mAb 216 + DNR | 0.38 | 92 |
| SUP B15 48 h | control | 5.7 | |
| | mAb 216 5 µg/ml | 4.3 | 24 |
| | ASPR 0.8 U/ml | 3 | 47 |
| | mAb 216 + ASPR | 2.3 | 60 |

VCR; vincristine,
DNR; Daunorubicin,
ASPR; asparginase

Example 7

Density of mAb 216 Receptors on B Lymphocytes

The density of the surface receptors to which mAb 216 binds on B lymphocytes was determined using standard procedures, as described briefly below. The pre-B cell line Nalm-6 and human splenic B lymphocytes were utilized. Briefly, MAb 216 was conjugated to fluorescein isothiocyanate (FITC, Molecular Probes, Inc.), and absorbance of the conjugated pure antibody was measured at 280 nm and 492 nm to determine the ratio of fluorophore to protein (F/P). The amount of FITC per molecule of 216 was calculated using the standard formula.

Cells were incubated with increasing concentration of conjugated antibody and labeled cells were analyzed using flow cytometry. The amount of antibody required to reach saturation was recorded. Using the fluorescein/protein (F/P) ratio, the molecules of receptors on the cell surface were calculated: Nalm-6 cells were found to express receptors at a density of about $2 \times 10^6$ receptors per cell and splenic B cells were found to express receptors at a density of about $1.34 \times 10^6$ receptors per cell on the cell surface. These densities are similar to those observed for the expression of CD8 on T cells. The cells of the Nalm-6 cell line are about one and half times larger in size than splenic B cells.

REFERENCES

1. Siiman, O and Burshteyn, A. (2000) "Cell surface receptor-antibody association constants and enumeration of receptor sites for monoclonal antibodies," *Cytometry* 40(4), 316-26.
2. http://www.drmr.com/abcon/FITC.html. FITC conjugation of antibodies.
3. http://www.cyto.purdue.edu/hmarchiv/1995/0979.htm. Antigen density.
4. http://iacf.bsd.uchicago.edu/FlowHome/Protocols/abconjugate.htm. Antibody conjugation.

Example 8

The Epitope for mAb216 is Associated with the Cytoskeleton

Cell surface receptors can remain associated with cytoskeletal structures after specific ligand binding, after cross linking by lectins, or in an unoccupied state. An association between the receptor and the cytoskeleton can be investigated by assessing the proportion of receptor that is not solubilized by non-ionic detergent NP-40 and remains associated with the insoluble cytoskeletal matrix. To determine if the CDIM epitope of B cells is associated with the cytoskeleton, the co-localization of mAb 216 binding with the insoluble cytoskeletal matrix of B cells was investigated using fluorescent and radiolabeled antibodies, as described below.

Methods:

Nalm-6 cells were labeled at 4° C. with biotinylated mAb 216, or with FITC conjugated anti-CD71 or FITC conjugated anti-CD19. FITC-labeled cells were washed twice, and resuspended in an extraction buffer containing 0.5% NP-40. Cells labeled with biotinylated mAb216 were washed twice and then stained with avidin-FITC, washed again, and resuspended in an extraction buffer containing 0.5% NP-40. The NP-40 treatment strips the cells of the detergent soluble membrane proteins, leaving behind the cytoskeletal matrix and intact nucleus. The intact stripped cells were analyzed by FACS or fluorescence microscopy.

MAb 216 directly conjugated with radioisotope $^{125}$I was incubated with the pre-B cell line Nalm-6 ($1 \times 10^6$ cells) for 15 minutes at 4° C. Following multiple washings, the cells were either homogenized mechanically or the membrane proteins solubilized using 0.5% NP-40. The material was then centrifuged at 6000×g for 15 minutes and the distribution of $^{125}$-mAb 216 determined in the sediment (which consisted primarily of the nucleus and associated cytoskeleton) and the supernatant (which consisted primarily of cell membrane and cytoplasm).

Results:

The fluorescence of antibodies binding the membrane associated antigens CD71 and CD19 on Nalm-6 cells due to FITC conjugated antibodies was abolished following this exposure to NP-40 buffer. However, the fluorescence intensity of mAb 216 bound to the B cell ligand did not change following detergent treatment.

In addition, most of the $^{125}$I-mAb 216 (80-85%) was found to be associated with the nuclear/cytoskeletal fraction after sedimentation. Very little mAb 216 was found in the cytoplasmic fraction where the majority of the membrane bound proteins are known to fractionate.

These data demonstrate that the anti-CDIM antibody, mAb 216, binds to an epitope that is associated with the cytoskeleton of the B cell.

Example 9

The Cytotoxicity of mAb 216 is Enhanced by Crosslinking

The in vitro cytotoxicity of mAb 216 to Nalm-6 cells was evaluated using PI staining and viability assessment (percent live cells) as a function of the amount of mAb 216 present. The amount of mAb 216 needed to achieve 50% and 80% viability in Nalm-6 cells with and without a crosslinking agent (a secondary mAb, e.g., anti-human lambda) is shown in Table 1, expressed in nanograms antibody required to achieve the indicated level of cytotoxicity, as determined by PI entry into cells.

These results demonstrate that cell viability is also influenced by the addition of a crosslinking agent, here a secondary antibody which binds to the IgM. As shown below, the addition of a crosslinking agent enhances the cytotoxicity of mAb 216 such that only half as much antibody is required to achieve 20% cell death (80% viability), and only 60% as much antibody is required to achieve 50% cell death (50% viability) in the presence of crosslinking antibody. The crosslinking agent appears to provide additional rigidity to the antibody-cell surface receptor complex to enhance the cell wounding and/or death.

TABLE 1

ED50 and ED80 values of mAb 216 with and without crosslinking

|  | ED50 | ED80 |
|---|---|---|
| With secondary Ab | | |
| Experiment #1 | 697.644 | 257.944 |
| Experiment #2 | 647.524 | 214.164 |
| Without secondary Ab | | |
| Experiment #1 | 1036.346 | 576.345 |

Example 10

The Cytotoxicity of mAb 216 is Enhanced by Crosslinking but the Cytotoxity of Rituxan is Not Enhanced by Crosslinking The in vitro cytotoxicity of mAb 216 and C2B8 (RITUXAN®) to OCI-Ly8 cells was evaluated using PI staining and viability assessment (percent live cells) of cells treated with mAb 216 and C2B8. OCI-Ly8 cells ($5 \times 10^5$ cells/ml) were treated overnight at 37° C. with 15 μg of each antibody in the absence of complement and effector cells. Secondary antibody (5 μg) was added to the appropriate samples (anti-IgG and anti-IgM). Cells were washed, resuspended in staining medium containing PI, and analyzed on Facscan. Cells were kept at 37° C. at all times.

Results

Figure 7:
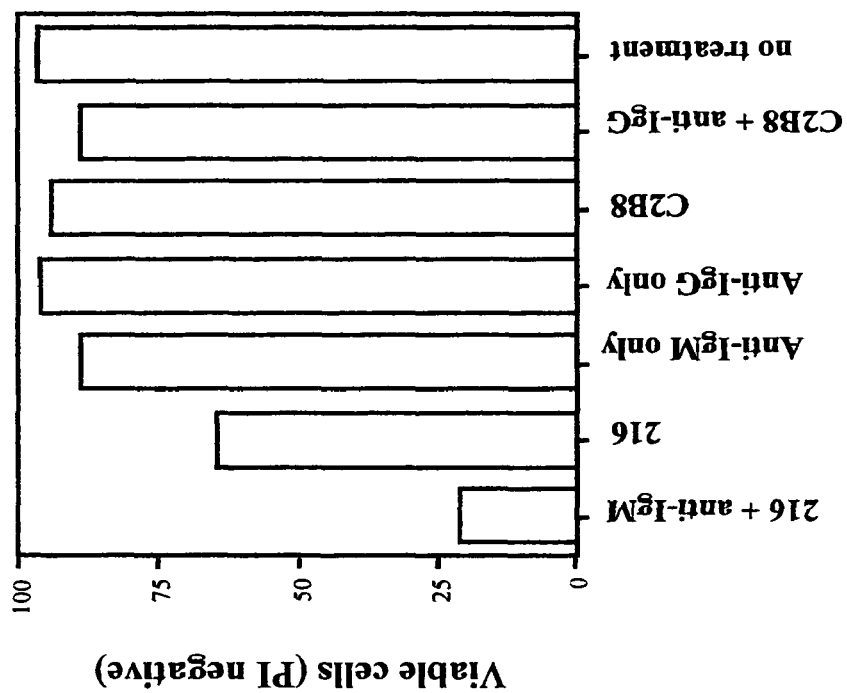
FIG. 7 illustrates the additional cytotoxicity of mAb when the antibody is crosslinked.

Viable cells (PI negative) in each sample are shown in FIG. 7. As shown in FIG. 7, the viability of cells treated with no antibody (control), and with the antibodies C2B8, anti-IgG, anti-IgM, and C2B8+anti-IgG, was similar, indicating that none of these treatments caused significant cytotoxicity in the absence of complement or effector cells. MAb 216 treatment without secondary antibody resulted in a viability of about 65%. In the presence of secondary antibody, the combination of mAb 216+anti-IgM resulted in a viability of only about 20%.

These results demonstrate a significant enhancement in cytotoxicity of mAb 216 (an IgM which possesses the capacity to crosslink antigens by virtue of its pentameric structure) which is due to additional crosslinking that occurred in the presence of the hypercrosslinking agent, anti-IgM.

Example 11

Dose Dependent Cytotoxicity of mAb 216 to Splenic B Cells and a B Cell Line

Titration of antibody into a cell suspension of Nalm-6 cells or splenic B cells (at $5 \times 10^5$ cells per ml) demonstrates the dose dependent cytotoxicity of mAb 216 to B cells. As shown in FIG. 8, as the amount of FITC conjugated antibody is increased, the amount of fluorescence detected using facscan increases rapidly, until all cell receptor sites are saturated with antibody. The binding curves of both cell types appear to be similar, exhibiting saturation at roughly the same concentration of antibody. However, the dependence of cell viability on mAb concentration varies significantly between the cell types. For example, at approximately 5 µg/ml antibody, splenic B cells exhibit a viability of about 65%. In contrast, Nalm-6 cells at the same concentration of antibody exhibit a viability of only about 42%. This amount of antibody is sufficient to provide at least a three fold excess to the total amount of CDIM epitopes on the Nalm-6 cells, and is closer to a five fold excess for the splenic B cells. At approximately 10 µg/ml antibody, splenic B cells exhibit a viability of about 48%, while Nalm-6 cells exhibit a viability of only about 30%. Thus, the B cell lines exhibit greater susceptibility to killing with the CDIM binding antibody than mature B lymphocytes, suggesting that neoplastic B cells are more susceptible to killing with mAb 216 than mature B cells.

Example 12

Efficacy of mAb 216 in Patients with ALL in Clinical Trials

This phase I dose escalation study of human mAb 216 was performed in adults with relapsed or refractory B-precursor ALL to preliminarily define the anti-tumor activity of mAb 216 within the confines of a phase I study; and to assess the biologic activity of mAb 216 in patients with relapsed or refractory ALL. Patients had previously been treated multiple times with Vincristine as part of a multidrug treatment program, but had become refractory to treatment with Vincristine, i.e., Vincristine treatment was not effective to reduce leukemic blast counts.

Antibody Administration: Day 0 and Day 7

The initial dose rate at the time of the first mAb 216 infusion was 25 mg/hour for the first half hour. If no toxicity or infusion-related event occurred, the dose rate was escalated (25 mg/hour increments at 30 minute intervals) to a maximum of 200 mg/hour, to a total dose of 1.25 mg/kg.

Disease Evaluation and Pharmacokinetics

Early response to therapy was performed on Day 7, prior to proceeding with the second antibody infusion. Patients received the second dose of antibody in conjunction with Vincristine.

Chemotherapy

Vincristine was given at a dose of 1.5 mg/m$^2$/dose IVP on Day 7 prior to initiating dose #2 of antibody.

Results

Patients treated with mAb 216 alone showed a decrease in WBC following the infusion of antibody. Patients subsequently treated with the combination of Vincristine and mAb216 showed a more dramatic decrease in WBC. These data are presented graphically in FIGS. 9A and 9B. Arrows indicate the days of administration of mAb 216, with and without Vincristine.

Figure 9A:
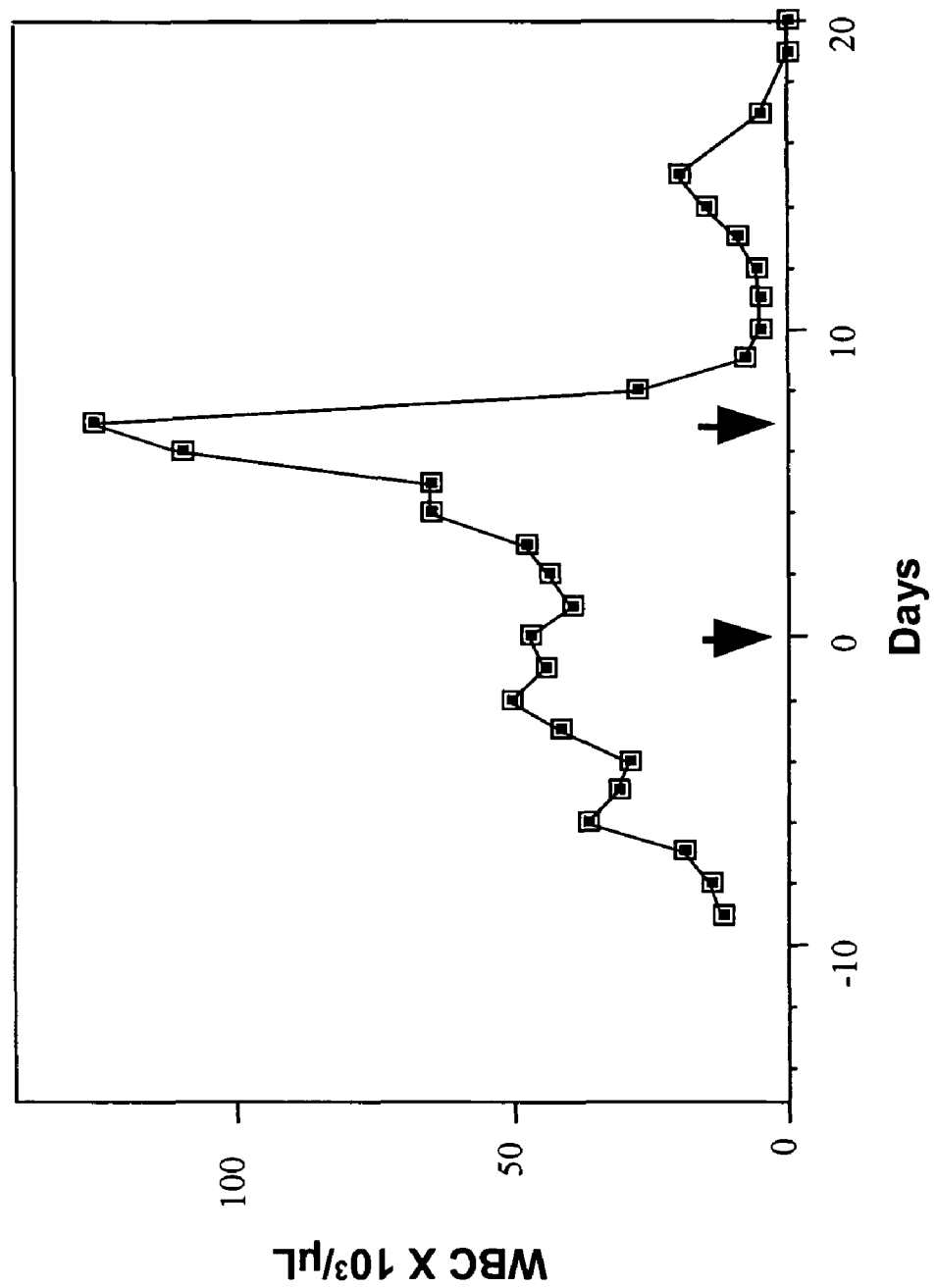
FIGS. 9A and B illustrate the efficacy of the treatment with mAb216 and Vincristine in human patients.

Patient 2 presented with 90-95% blasts in peripheral blood and bone marrow, and a rising WBC count. Treatment with 1.25 mg/kg mAb216 alone resulted in a transient decrease in WBC count, and by day 7, WBC counts were elevated again to greater than $10^5$ WBC per µL. Treatment with 1.25 mg/kg mAb216 in combination with Vincristine at 1.5 mg/m$^2$/dose IVP resulted in a dramatic decrease in WBC. The results are shown in FIG. 9A.

Figure 9B:
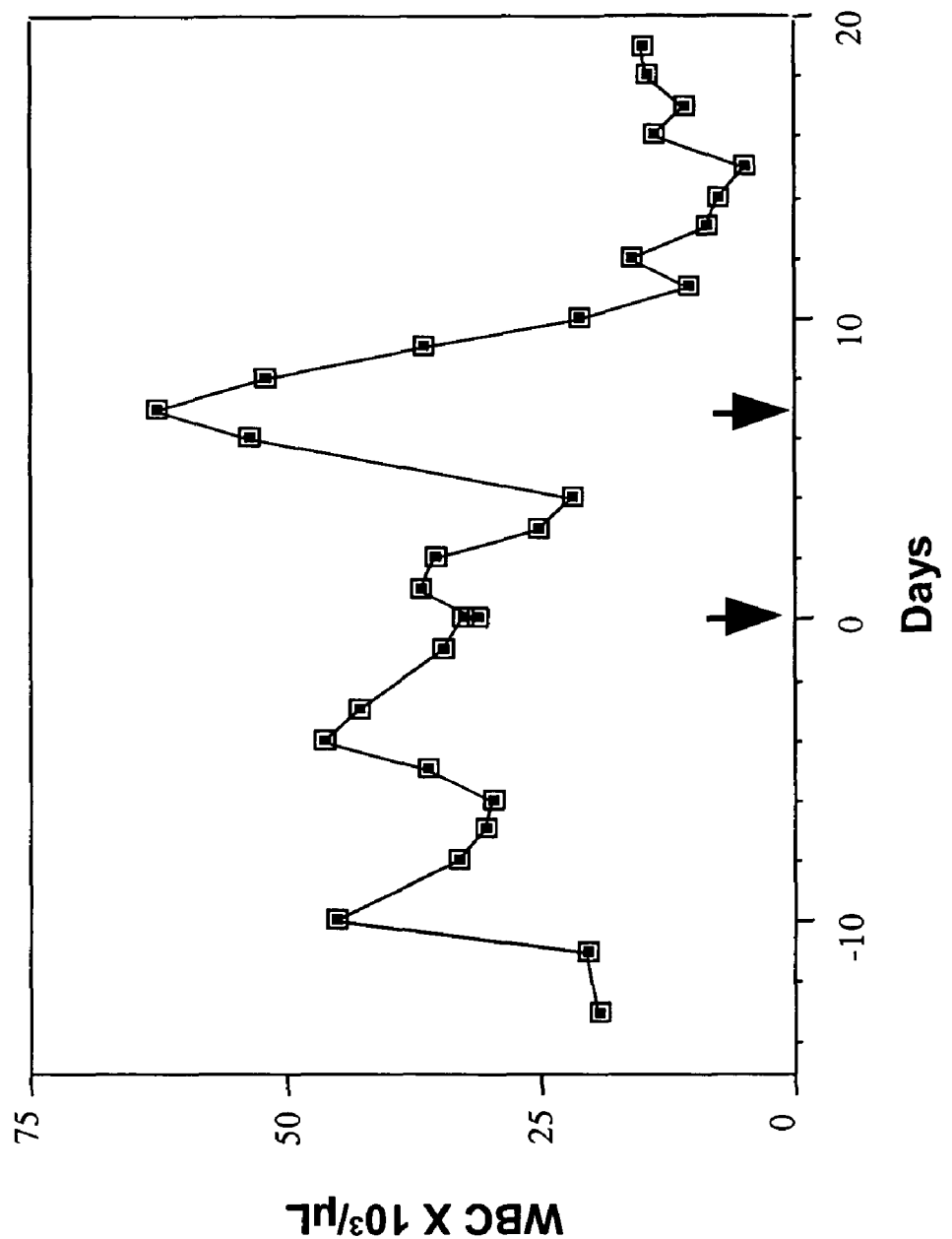

Patient 3 presented with 90-98% blasts in peripheral blood and bone marrow, and a WBC count of about 40,000 WBC/ µL. Treatment with 1.25 mg/kg mAb216 alone resulted in a transient decrease in WBC count, and by day 7, WBC counts were elevated again. Treatment with 1.25 mg/kg mAb 216 in combination with Vincristine at 1.5 mg/m$^2$/dose IVP again resulted in a dramatic decrease in WBC. The results are shown in FIG. 9B.

These data demonstrate that the combination of chemotherapeutic treatment with mAb 216 results in surprising and synergistic efficacy in human patients suffering from ALL. It is demonstrated that WBC become more susceptible to treatment with chemotherapeutic agents due to treatment with mAb 216, even at sublethal concentrations of the antibody, enhancing the efficacy of treatments with additional chemotherapeutic agents.

What is claimed is:

1. A method of treating a mammal suffering from a condition characterized by hyperproliferation of B cells, wherein said hyperproliferating B-cells are cancer cells, comprising administering a cell membrane-wounding VH4-34 antibody that binds to the CDIM epitope on the surface of B cells, in combination with a second cytotoxic agent, wherein said cell membrane wounding VH4-34 antibody is administered at a dosage that was determined to cause membrane pores that allow the second cytotoxic agent to enter said hyperproliferating B-cells to synergistically reduce viability of said hyperproliferating B cells.

2. The method of claim 1, wherein the mammal is a human.

3. The method of claim 1, wherein the mammal is a non-human mammal.

4. The method of claim 1, wherein the hyperproliferating B cells are stimulated into a hyperproliferating condition by growth factors, cytokines, or Epstein Barr Virus infection.

5. The method of claim 1, wherein the second cytotoxic agent is a chemotherapeutic agent, a radioactive isotope, a cytotoxic antibody, an immunoconjugate, a ligand conjugate, an immunosuppressant, a cell growth regulator or inhibitor, a toxin, or mixtures thereof.

6. The method of claim 5, wherein the chemotherapeutic agent is vincristine, daunorubicin, L-asparaginase, or colchicine.

7. The method of claim 1, wherein the condition characterized by a hyperproliferation of B cells is lymphoid cancer.

8. The method of claim 1, wherein the viability of hyperproliferating B cells is reduced to 42 percent.

9. The method of claim 1, wherein the viability of hyperproliferating B cells is reduced to 30 percent.

10. The method of claim 1, wherein said cell membrane wounding VH4-34 antibody is administered at a dosage of 1.25 mg/kg bodyweight.

11. A method of killing neoplastic B cells in a mammal, comprising administering to neoplastic B cells a cytotoxic amount of a cell membrane wounding VH4-34 antibody that binds to the CDIM epitope on the surface of the neoplastic B cells in combination with a second cytotoxic agent, wherein said cell membrane wounding VH4-34 antibody is administered at a dosage that was determined to cause membrane pores that allow the second cytotoxic agent to enter said neoplastic B cells to synergistically reduce the viability of the neoplastic B cells.

12. The method of claim 11, wherein the mammal is a human.

13. The method of claim 11, wherein the mammal is a nonhuman mammal.

14. The method of claim 11, wherein the neoplastic B cells are stimulated into a hyperproliferating condition by growth factors, cytokines, or Epstein Barr Virus infection.

15. The method of claim 11 wherein the second cytotoxic agent is a chemotherapeutic agent, a radioactive isotope, a cytotoxic antibody, an immunoconjugate, a ligand conjugate, an immunosuppressant, a cell growth regulator or inhibitor, a toxin, or mixtures thereof.

16. The method of claim 11, wherein the second cytotoxic agent is vincristine, daunorubicin, L-asparaginase, or colchicine.

17. The method of claim 11, wherein the mammal has lymphoid cancer.

18. The method of claim 11, wherein the viability of neoplastic B cells is reduced to 42 percent.

19. The method of claim 11, wherein the viability of neoplastic B cells is reduced to 30 percent.

20. The method of claim 11, wherein said cell membrane wounding VH4-34 antibody is administered at a dosage of 1.25 mg/kg bodyweight.

* * * * *